(12) United States Patent
Usami et al.

(10) Patent No.: US 6,610,046 B1
(45) Date of Patent: Aug. 26, 2003

(54) CATHETER AND GUIDE WIRE

(75) Inventors: Shino Usami, Tokyo (JP); Nobuko Usami, Tokyo (JP); Akino Usami, Tokyo (JP); Gono Usami, Tokyo (JP); Kaya Usami, Tokyo (JP); Tomono Usami, Tokyo (JP); Masano Usami, Tokyo (JP); Nano Usami, Tokyo (JP); Keiko Usami, Tokyo (JP)

(73) Assignee: USAminanotechnology Inc., Tokyo (JP)

( * ) Notice: Subject to any disclaimer, the term of this patent is extended or adjusted under 35 U.S.C. 154(b) by 0 days.

(21) Appl. No.: 09/720,677

(22) PCT Filed: Apr. 27, 2000

(86) PCT No.: PCT/JP00/02777

§ 371 (c)(1),
(2), (4) Date: Dec. 29, 2000

(87) PCT Pub. No.: WO00/66211

PCT Pub. Date: Nov. 9, 2000

(30) Foreign Application Priority Data

| Apr. 30, 1999 | (JP) | 11-124234 |
| Jun. 18, 1999 | (JP) | 11-172363 |
| Jun. 18, 1999 | (JP) | 11-172364 |
| Nov. 9, 1999 | (JP) | 11-317949 |

(51) Int. Cl.$^7$ ............................................. A61M 25/00
(52) U.S. Cl. ...................... 604/530; 604/264; 606/194; 600/585
(58) Field of Search ................................ 604/264, 523, 604/525, 530, 531, 532; 606/194; 600/585

(56) References Cited

U.S. PATENT DOCUMENTS

| 5,231,989 A | * | 8/1993 | Middleman et al. | 128/657 |
| 5,334,168 A | * | 8/1994 | Hemmer | 604/281 |
| 5,531,719 A |   | 7/1996 | Takahashi | 604/280 |
| 5,597,378 A | * | 1/1997 | Jervis | 606/78 |
| 5,601,539 A | * | 2/1997 | Corso, Jr. | 604/282 |
| 5,782,811 A |   | 7/1998 | Samson et al. | 604/282 |
| 5,906,606 A |   | 5/1999 | Chee et al. | 604/527 |
| 6,165,292 A | * | 12/2000 | Abrams et al. | 148/563 |
| 6,251,104 B1 | * | 6/2001 | Kesten et al. | 606/15 |

FOREIGN PATENT DOCUMENTS

| JP | 60-187737 | 12/1985 |
| JP | 61-115550 | 6/1986 |
| JP | 3-188875 | 8/1991 |
| JP | 4-108555 | 9/1992 |
| JP | 6-134034 | 5/1994 |
| JP | 7-008560 | 1/1995 |
| JP | 7-096036 | 4/1995 |
| JP | 7-096037 | 4/1995 |
| JP | 8-257128 | 10/1996 |
| JP | 8-308933 | 11/1996 |
| JP | 8-308934 | 11/1996 |
| JP | 408308934 A | * 11/1996 |
| JP | 9-094296 | 4/1997 |
| JP | 9-266949 | 10/1997 |
| JP | 10-071208 | 3/1998 |
| JP | 11-009695 | 1/1999 |

OTHER PUBLICATIONS

Shape Memory Applications, 1999, Internet NiTi Smart Sheet, pp. 9.*
Middle East Technical University, Internet Pseudoelasticity of Shaped Memory Alloys, pp. 3.*

* cited by examiner

*Primary Examiner*—Charles G. Freay
*Assistant Examiner*—John F. Belena
(74) *Attorney, Agent, or Firm*—Birch, Stewart, Kolasch & Birch, LLP

(57) ABSTRACT

A catheter and guide wire in which at least a distal end portion of a catheter body or guide wire is formed of a shape memory-specialized metal having shape memory property, but free from superelasticity or pseudoelasticity at least at the body temperature, have high safety and improved operability as compared with prior art ones and are advantageously used in a wide range of examination and treatment, especially in angiography, angioplasty, embolization, foreign matter removal and recovery, calculus capture and so on.

8 Claims, 24 Drawing Sheets

FOUR SLITS | TWO SLITS | NO SLITS

CATHETER AND GUIDE WIRE

This application is the national phase under 35 U.S.C. §371 of PCT International Application No. PCT/JP00/02777 which has an International filing date of Apr. 27, 2000, which designated the United States of America.

BACKGROUND OF THE INVENTION

1. Field of the Invention

This invention relates to a medical catheter and guide wire which have high safety and improved operability and are advantageously used in a wide range of examination and treatment, especially in angiography, angioplasty, embolization, retriever/recovery of foreign body, and calculus capture.

2. Prior Art

Conventional catheters designed to be inserted into blood vessels and ureters for examination and treatment purposes include, for example, those used in angiography, intravascular medicament administration, intravascular surgery, ureterolithotomy, and endoscopic retrograde cholangiopancreatography (ERCP).

There have been proposed several catheters of this type including a tube of a flexible polymer having a leading metallic guide wire inserted therein, a tube of polyethylene having stainless steel wire braided in a mesh fashion, and a helically cut stainless steel tube enclosed in a synthetic resin (see JP-A 6-134034 and JP-A 7-96037).

However, in all cases of these conventional catheters, it has been difficult for operators to smoothly insert and guide them into complex and tortuous thin wall vessels and ureter to the target sites. Also, since they do not possess enough flexibility, suppleness, elasticity, and operability and other characteristics required for catheters, they always need the combined use of leading guide wires to complement the characteristics required for catheter bodies.

On the one hand, JP-A 8-257128 proposes a medical tube whose structure is shown in FIG. 37. It consists of a metal tube "a," made of stainless steel, shape memory alloy, and the like, which has a groove or grooves shown as "b" on its distal end. The grooves are engraved into the shape of either a helix as a whole, or circles spaced apart at certain intervals, and may be separated at some points or other by connection regions without grooves. The outer surface of tube "a" is covered with a resin coating or resin tube "c."

Furthermore, JP-A-8-308933 proposes a medical tube whose structure is shown in FIG. 38. It consists of a metal tube "a," whose distal portion is thinner-walled as compared with a proximal portion. The said distal portion has a groove or grooves "b," which are engraved into the shape of either a continuous helix, or a helical shape as a whole, or circles spaced apart at certain intervals, and which may be separated at some points or other by connection regions without grooves. The outer surface of the said tube "a" is covered with a resin coating or resin tube "c."

In these medical tubes, the radial or helical grooves in the distal portion confer some degree of flexibility, but not to a satisfactory extent. When the tubes are advanced into complex tortuous blood vessels and ureters, the distal portion can break or fail. Additionally, the outer resin tube or resin coating can be caught in the grooves. In particular, the metal tube whose distal portion is thinner-walled as in JP-A 8-308933 can be more readily broken. These medical tubes are thus not satisfactory in terms of safety and operability.

Moreover, JP-A 3-188875 discloses a catheter comprising a body portion and a distal portion with an internal lumen wherein at least the said body portion is made of a superelastic metal tube.

However, since this catheter has superelastic effect due to the superelasticity of the said metal tube, the problem of blood vessel damages such as rupture, perforation, dissection and so on may arise. This is because if the distal portion is brought into contact with a part of the blood vessel and applies inadvertent force there, it will deform the vessel, and when the stress is removed, due to the superelasticity of the tube, it will immediately recover the original state resulting in the damages of the said blood vessel.

To solve this problem, a catheter has been proposed in which a leading tube formed mainly of a thermoplastic polymer and of several millimeters to several centimeters long is attached to the distal end of a conventional catheter.

The catheter having the said thermoplastic tube attached to the distal end, however, has a step-like structure at the boundary between the thermoplastic resin tube at the distal end and the metallic catheter body trailing the rear end of the tube, resulting in losses of operability and safety.

Specifically, the catheter having a leading tube by thermoplastic resin at the distal end does not exhibit fully satisfactory performance where the boundary between the thermoplastic resin tube at the distal end and the metallic catheter body trailing the rear end of the tube contacts against the wall of a complex tortuous blood vessel or ureter. The distal portion made of the flexible thermoplastic resin can enter the sharply bent blood vessel or ureter, but the subsequently advancing boundary with the metallic catheter body comes in contact with the blood vessel wall, whereby the distal portion of the catheter can broken or damaged at the boundary. This causes pain or abnormal feeling and sometimes can cause damage to the sensitive blood vessel or ureter.

Recently, in the treatment of arteriovenous malformation (AVM), embolization using an embolic material such as isobutyl cyanoacrylate (IBCA), n-butyl cyanoacrylate (NBCA) or ethylene-vinyl alcohol copolymer (EVAL) has achieved favorable results without hemorrhage. A great attention is paid to this embolization.

However, the embolization using an embolic material gives rise to a problem associated with injection of the embolic material. Since the embolic material is injected from the distal outlet of the catheter without blocking the blood flow, the embolic material can solidify in a state bonded to the catheter distal end, which prevents withdrawal of the catheter.

Further, up to the present, the only method for blocking blood flow for treatment purposes which can be used in practice is the use of a balloon catheter having a balloon attached to the distal end thereof.

For the blockage of blood flow using a balloon catheter, there is known a method involving heat fusing a balloon made of such material as silicone rubber, latex, or the like, to the distal end of a catheter, and injecting saline containing a contrast medium into the balloon through the catheter body to inflate the balloon at the distal end of the catheter to block the blood flow. Alternatively, a flowpath for injecting saline containing a contrast medium may be provided separately from the catheter body, and saline containing a contrast medium is injected into the balloon through the flowpath to inflate the balloon to block the blood flow.

However, the said balloon catheter with a separate flowpath results in a larger diameter which makes it difficult for the operator to insert it smoothly into a narrow blood vessel, ureter, pancreatic duct or bile duct (with a diameter of less than 2 mm). Also, because of structural restrictions of the balloon catheter, it is impossible to discharge the embolic material or contrast medium from the distal end of the catheter while blocking the blood flow.

There has been an embolization treatment wherein a guide wire having a distal head with a large diameter or a dilated projection is inserted into the catheter lumen for pushing out and implanting an embolic material such as a coil and the like at the target site.

However, when the above method is applied to a complex tortuous thin wall blood vessel, ureter, pancreatic duct or bile duct, it is sometimes impossible to smoothly insert the guide wire or to implant an embolic material such as a coil at the target site because the catheter body and guide wire may have strong rebounding or repulsive forces and lack flexibility.

Furthermore, as a catheter for retrieving and recovering foreign matter and a catheter for capturing calculus in the kidney or ureter, there has recently been proposed a catheter in which an operating part (or guide wire) having a foreign matter retrieving/recovering means or calculus capturing means at its distal end is inserted through its lumen (see JP-A 61-115550).

The said foreign matter retrieving/recovering and calculus capturing catheters lack flexibility and possess a strong restoring force because their catheter body is formed of a resinous tube or a metallic tube of stainless steel or superelastic metal. The operating part (or guide wire) trailing the foreign matter retrieving/recovering means or calculus capturing means also possesses strong rebounding or repulsive forces and lacks flexibility. As a result, when the above catheter is applied to a complex tortuous thin wall ureter, it is difficult to smoothly insert the catheter and carry the foreign matter retrieving/recovering means or calculus capturing means to the destination, failing to take full advantage of the foreign matter retrieving/recovering means or calculus capturing means.

As described above, the catheters and guide wires used in a wide range of examination and treatment, especially in embolization, angioplasty, angiography, retrieving/recovering of foreign matter, and calculus capture have several problems. It is desired to have a catheter and guide wire which facilitate a wide range of examination and treatment in a more safe and reliable manner.

SUMMARY OF THE INVENTION

The present invention has been made under the above-described circumstances, and its primary object is to provide a catheter which is constructed such that a catheter body has a distal portion and a proximal portion, at least the distal portion being free from superelasticity or pseudoelasticity while retaining the shape memory property, the proximal portion having rigidity, whereby the catheter has flexibility, suppleness and elasticity sufficient for eliminating a need for a leading guide wire for manipulation, resulting in improved safety and operability.

A second object of the invention is to provide a catheter which eliminates any step-like structure at the junction between a leading tube made of thermoplastic resin and a catheter body, minimizing the induction of unusual feeling and pain, and preventing damages of a blood vessel during operation as much as possible.

A third object of the invention is to provide a catheter which can be smoothly inserted into even a complex tortuous thin wall vessel, ureter, pancreatic duct or bile duct, ensures to block the blood or fluid flow at the destination, and enables angiography of blood vessels or embolization of lesions in a safe and reliable manner while maintaining the blocking of the blood flow.

A fourth object of the invention is to provide a catheter whose body has slits so that the body is formed as one-piece from the distal end to the proximal end eliminating the need for a leading tube made of thermoplastic resin, without a step-like structure, is unlikely to be broken, is improved in operability and safety, and is improved in manufacture cost performance in that the catheter diameter can be readily adjusted in accordance with the size of the destination.

A fifth object of the invention is to provide a catheter and a guide wire whose combination is effective for carrying out embolization, angiography, and foreign matter retrieval/recovery in a safe and reliable manner.

To attain the above objects, the present invention provides the catheter and guide wire defined below.

A first aspect provides a catheter characterized in that at least a distal end portion of a catheter body is formed of a shape memory-specialized alloy which has been so manufactured that it retains shape memory property, but free from superelasticity or pseudoelasticity at least at the body temperature.

In the catheter according to the first aspect of the invention, since at least the distal end portion of the catheter body is formed of a shape memory-specialized alloy and deprived of a strong repulsive force due to superelastic or pseudoelastic effect, the catheter can be safely and smoothly inserted in conformity with the shape of a blood vessel at the destination owing to the shape memory, eliminating the possibility of damages of a blood vessel which would have been caused by the distal end portion of a catheter body if it had superelasticity or pseudoelasticity.

A second aspect provides a catheter comprising a catheter body, an outer polymer layer covering the outer surface of the catheter body, and a thermoplastic resin tube joined to the distal end of the catheter body, characterized in that the region extending from the distal end portion of the catheter body to at least a proximal end portion of the thermoplastic resin tube, is reinforced by winding and/or braiding a linear elastic material selected from among a metal wire, organic wire and inorganic wire, either in a mesh fashion or in a coil fashion, respectively, or attaching the linear elastic material along the axial direction, or any combination of the above.

According to the second aspect of the invention, the catheter eliminates any step-like structure at the junction between the leading tube made of thermoplastic resin and the catheter body, minimizes the induction of unusual feeling and pain, and prevents a blood vessel from being damaged during operation as much as possible.

A third aspect provides a catheter comprising a catheter body and an outer polymer layer covering the outer surface of the catheter body, characterized in that the outer polymer layer is projected forward, and the catheter body is provided at a distal end with an injection part having lumen perforated therein, wherein the forward projection of the outer polymer layer can be radially dilated by injecting an injection fluid such as saline, an embolic material or a contrast medium through the lumen into the interface between the injection part and the forward projection of the outer polymer layer to fill the interface therewith.

Unlike the prior art balloon catheter having an inflating balloon at the distal end, the catheter according to the third aspect of the invention is provided with an inflating space or gap within the distal end portion of the catheter itself wherein by injecting an injection fluid such as saline, an embolic material or a contrast medium into the space or gap, the distal end portion of the catheter is dilated outward. This eliminates the need for an extra balloon and a separate conduit for inflating the balloon, allows the catheter to be formed thin, and enables to block the blood flow and the like in a safe and reliable manner.

A fourth aspect provides a catheter comprising a catheter body and an outer polymer layer covering the outer surface of the catheter body, characterized in that the catheter body is provided with at least one slit extending axially from the distal end of the catheter body, and the gap of the slit is narrowed such that the catheter body is reduced in diameter toward the distal end.

The catheter according to the fourth aspect of the invention eliminates the need for a leading tube made of thermoplastic resin at the distal end or a step-like structure, is unlikely to be broken, is improved in operation and safety, and permits the catheter diameter to be readily adjusted in accordance with the size of the destination.

A fifth aspect provides a guide wire comprising a guide wire body and a distal head and adapted to be inserted into a catheter lumen, characterized in that the distal head of the guide wire is configured to a shape capable of pushing out an embolic material such as a coil, and at least a distal end portion of the guide wire body is formed of a shape memory-specialized alloy having shape memory property, but free from superelasticity or pseudoelasticity at least at the body temperature.

Since at least the distal portion of the guide wire body is formed of a shape memory-specialized alloy having shape memory property, but free from superelasticity or pseudoelasticity at least at the body temperature, the guide wire according to the fifth aspect of the invention can be smoothly inserted into even a complex tortuous thin wall vessel without the risk of the guide wire caught by the catheter lumen. This ensures that the expanded distal head pushes out an embolic material such as a coil so that the embolic material may be implanted at the destination within the living body.

BRIEF DESCRIPTION OF THE DRAWINGS

FIG. 14(B) showing the distal end portion of the catheter being dilated; and FIG. 14(C) showing the catheter having a lid which is provided with discharge lumen for providing communication between the space and the outside.

FIG. 17 illustrates a method for fabricating a catheter of the present invention.

FIG. 28 illustrates one exemplary method of forming a catheter with slits according to the invention.

DESCRIPTION OF THE PREFERRED EMBODIMENT

First Embodiment of the Invention

Figure 1A:
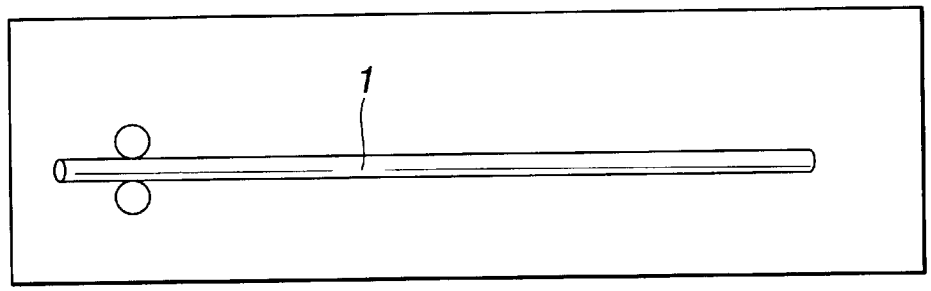
FIGS. 1(A) to (C) illustrate a bending test method.

The catheter according to the first embodiment of the invention is characterized in that at least a distal end portion of a catheter body is formed of a shape memory-specialized alloy having shape memory property, but free from superelasticity or pseudoelasticity at least at the body temperature. Thereby, a medical catheter which is improved in operation and safety and best suited for the examination and treatment of a blood vessel, ureter, pancreatic duct and bile duct, is obtained.

Conventional shape memory alloys, for example, Ni—Ti alloys are known to have two properties, superelastic property (also known as pseudoelastic property) and shape memory property associated with the reverse transformation of thermoelastic martensitic transformation. The shape memory property is such nature that after the Ni—Ti alloy undergoes apparent plastic deformation, the alloy recovers the original shape upon heating the alloy to the so-called reverse transformation temperature. The superelastic or pseudoelastic property, on the other hand, is such nature that after a stress load is applied to the Ni—Ti alloy at a temperature above the reverse transformation temperature to impart apparent plastic deformation, the alloy completely recovers its shape at the instant of the stress removal.

The inventor has found that among the two natures of shape memory alloy, it is very advantageous for a catheter to be inserted into a sensitive, tortuous site such as a blood vessel to have shape memory property, while it is disadvantageous for the catheter to have superelastic or pseudoelastic property at the body temperature.

More particularly, when the catheter is inserted into a complex tortuous, sensitive blood vessel or similar duct, the use of a catheter body made of a shape memory alloy tube having both of the above two natures gives rise to the following problem. When the distal end of the catheter comes in abutment with the complex tortuous blood vessel wall, the distal end may deform and might be able to enter the sharply bent blood vessel. However, because of the strong restoring force due to superelastic effect, a strong force is applied to the blood vessel by virtue of that hard restoring force, resulting in possible damages to the blood vessel or ureter (e.g., rupture, perforation and dissection of blood vessel or ureter).

Further continuing the extensive investigation, the inventor has found the following. At least a distal end portion of a catheter body made of shape memory alloy is treated with heat or the like, so that the shape memory alloy may lose the superelastic or pseudoelastic property at the body temperature (in the present invention, this alloy is designated as "shape memory-specialized alloy"). Then, when certain stress is applied to the catheter within a blood vessel, the distal end portion is readily collapsed or bent and does not immediately exert the restoring force whereby the risk of damaging the blood vessel wall is minimized. Additionally, since the shape memory property of the shape memory alloy is fully retained, the catheter gradually restores the original shape in a natural way even after the catheter is collapsed or bent within the blood vessel or ureter under an inadvertent force.

The physical phase regions where the superelastic effect develops and the region where the shape memory effect develops are not necessarily the same. In the region around the possible body temperature, the set temperature (A) for the alloy to develop the superelastic effect differs from the set temperature (B) for the alloy to develop the shape memory effect. If the set temperature (A) developing the superelastic effect is 90° C., then the heat treating conditions can be set such that the alloy may become soft and develop the shape memory effect near 37° C. If the set temperature (A) developing the superelastic effect is near 37° C., then the set temperature (B) developing the shape memory effect would become lower than that, which would be inadequate to the objects of the invention. Also in the latter case, a region where both the superelastic effect and the shape memory effect develop would exist between the set temperature (A) developing the superelastic effect and the set temperature (B) developing the shape memory effect. When the catheter body is deformed around the body temperature, the catheter will restore its original shape upon release of the deforming force. With respect to the determination whether this restoring force is due to the superelastic effect or the shape memory effect, it is regarded that if the shape is restored in less than 0.3 second, the superelastic effect is predominant. Actually, in the case of instantaneous restoration in less than 0.3 second, there is a high probability that due to this strong elasticity, the blood vessel or ureter is damaged during operation of the catheter, according to the inventor's finding.

Figure 1B:
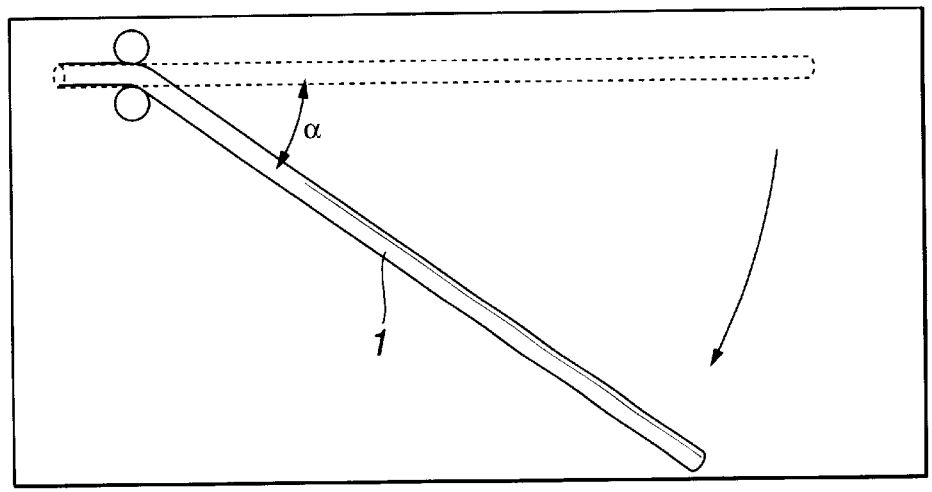
Figure 1C:
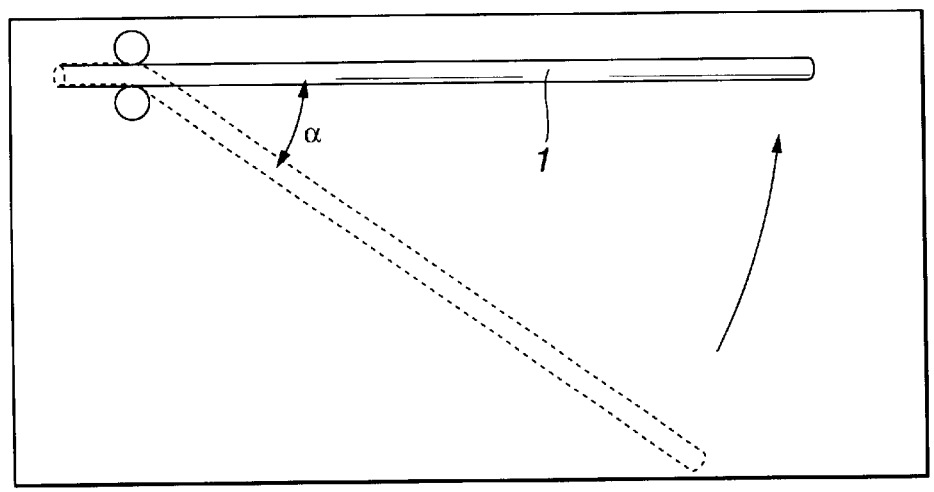

As used herein, the term "shape memory-specialized alloy free from superelasticity or pseudoelasticity at the body temperature" means that the set temperature developing superelasticity and the region where both superelastic effect and shape memory effect develop fall in a temperature region above the body temperature. With one end of a catheter body 1 fixed as shown in FIG. 1(A), at least a distal end portion (at least a portion extending 5 mm from the distal end, and especially a portion extending 30 cm from the distal end) of the catheter body 1 is deformed at an angle alpha of 30 to 90 degrees, preferably 45 to 90 degrees at the body temperature (typically about 33 to 42° C., preferably in the range of 35 to 38° C.) (see FIG. 1(B)). Upon release of the deforming force, the catheter body does not instantaneously or rapidly recover due to superelasticity or pseudoelasticity, but moderately or gradually recover due to shape memory effect as shown in FIG. 1(C). This restoring force is represented by a time of not shorter than 0.3 second, preferably not shorter than 0.5 second, more preferably not shorter than 1 second, further preferably not shorter than 1.5 seconds, and most preferably not shorter than 2 seconds. This is what is meant by the above term.

Further making extensive investigations on the shape memory property of the catheter body from a different aspect than the time of recovery, the inventor has found that the term "free from superelasticity or pseudoelasticity at the body temperature" can be also described in terms of the yield force, recovery force and residual strain in a three-point bending test.

Figure 2:
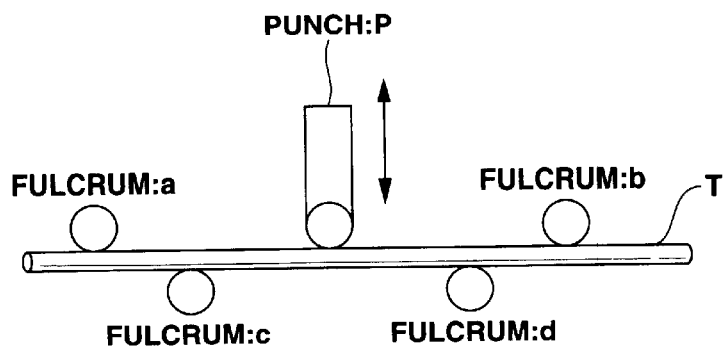
FIG. 2 is a schematic view illustrating the measurement method of a three-point bending test.
Figure 3:
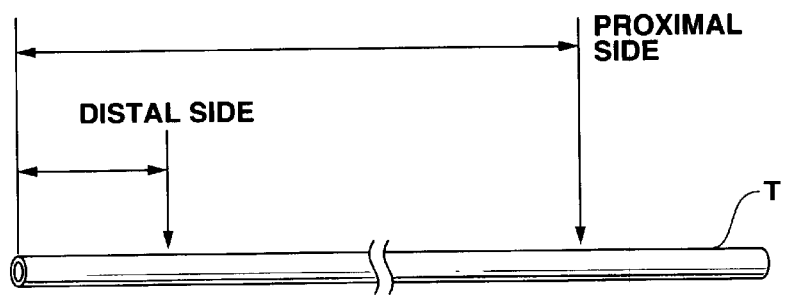
FIG. 3 is a schematic view showing the measurement site of FIG. 2.
Figure 5:
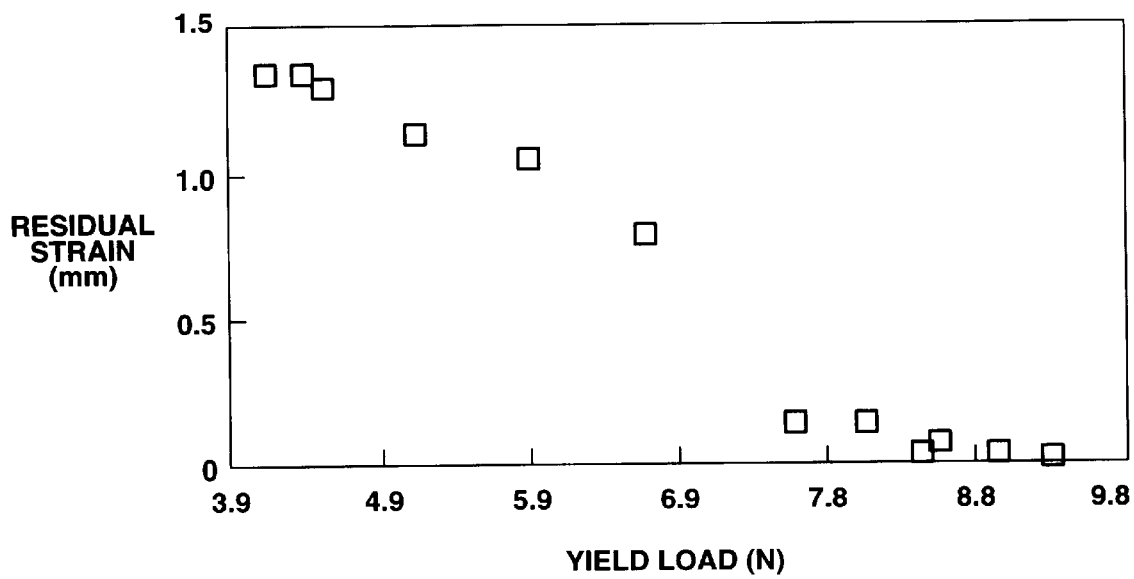
FIG. 5 is a graph showing residual strain versus yield force.
Figure 6:
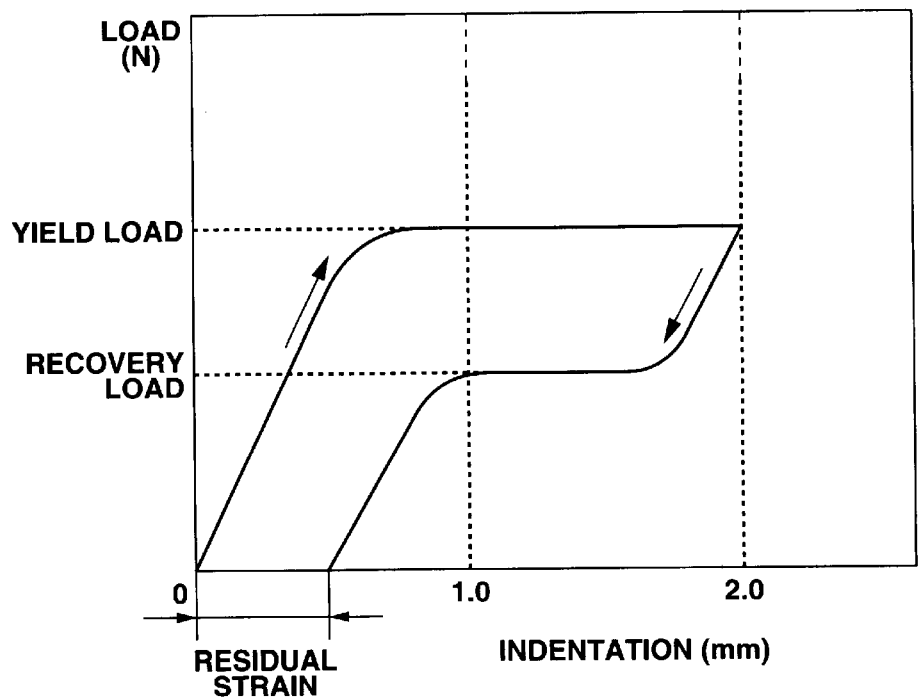
FIG. 6 is a diagram showing yield force and recovery force versus residual strain.

Specifically, as shown in FIG. 2, a metal tube T having both superelastic property and shape memory property or only shape memory property and having an outer diameter of 875 μm and an inner diameter of 750 μm is supported by a holder at fulcrums "a" to "d." Under the measurement conditions shown below, the yield force, recovery force and residual displacement after load release (from which the residual strain is determined) were determined at each point of measurement at a displacement of 1 mm as shown in FIG. 3. As a result, relationships as shown in FIGS. 4 to 6 are found among the yield force, recovery force and residual strain.

| Measurement conditions | |
| --- | --- |
| Test speed: | 2 mm/min. |
| Punch tip shape: | 5 mm diameter |
| Fulcrum shape (a to d): | 6 mm diameter |
| Fulcrum distance (a–b): | 18 mm |
| Fulcrum distance (c–d): | 14 mm |
| Punch displacement: | 2 mm |
| Measurement temperature: | 37 ± 1° C. |

Figure 4:
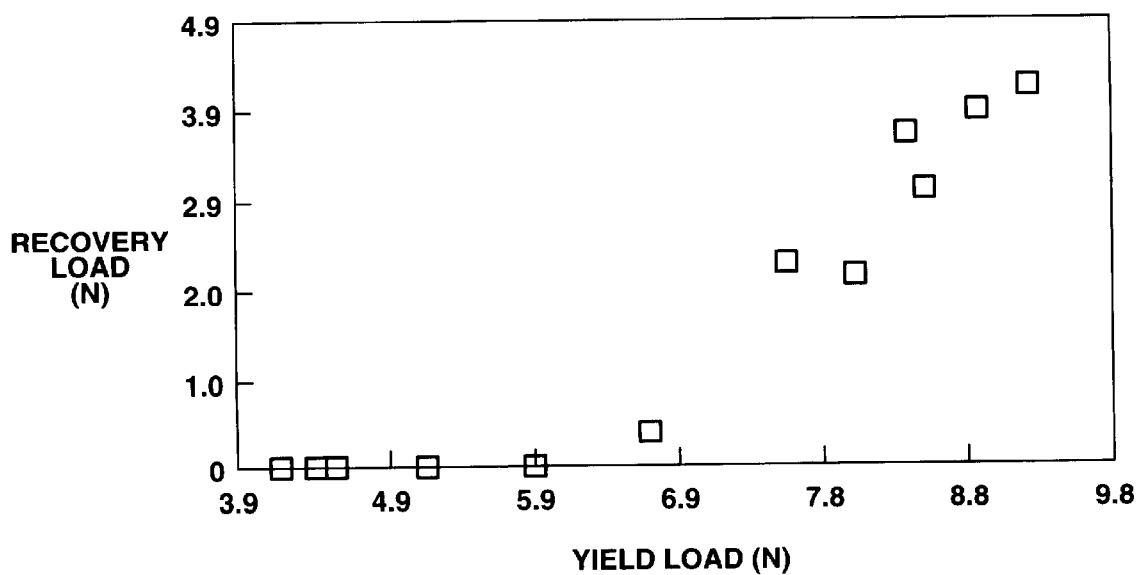
FIG. 4 is a graph showing recovery force versus yield force.

It is seen from FIG. 4 that the recovery force is approximately proportional to the yield force when the yield force is higher than about 5.9 N. It is seen from FIG. 5 that the residual strain is approximately inversely proportional to the yield force when the yield force is not higher than 8.8 N. That is, the greater the yield force, the greater becomes the recovery force and the less becomes the residual strain. It has also been found that when the yield force is not higher than 8.8 N, the recovery force is not higher than 2.9 N. and the residual strain is not lower than 0.2 mm, the deformed state can be maintained, strong return upon displacement can be prevented, that is, no superelastic or pseudoelastic effect is exerted.

Through actual testing, the inventor has found that the yield force, recovery force and residual strain of a distal end portion (at least a portion extending 5 mm from the distal end, and especially a portion extending 30 cm from the distal end) of the catheter body in the three-point bending test are outside the above range, strong superelastic or pseudoelastic effect develops to produce a strong restoring force, by which the blood vessel or ureter can likely be damaged during catheter operation.

Specifically, the term "shape memory-specialized alloy free from superelasticity or pseudoelasticity at the body temperature" as used herein means that the set temperature developing superelasticity and the region where both superelastic effect and shape memory effect develop fall in a temperature region above the body temperature, and when at least a distal end portion (at least a portion extending 5 mm from the distal end, and especially a portion extending 30 cm from the distal end) of the catheter body is deformed at least at the body temperature and the deforming force is released (or the operator loses hold during catheter operation), the restoration takes a time of not shorter than is 0.3 second, preferably not shorter than 0.5 second, more preferably not shorter than 1 second, further preferably not shorter than 1.5 seconds, and most preferably not shorter than 2 seconds. Herein, at least the distal end portion of the catheter body is preferably formed of a metal material which exhibits a yield force of not higher than 8.8 N, a recovery force of not higher than 2.9 N, and a residual strain of not smaller than 0.2 mm when a three-point bending test is carried out on a metal tube having an outer diameter of 875 μm and an inner diameter of 750 μm.

More particularly, the preferred range of the yield force, recovery force and residual strain in the three-point bending test is given below since the preferred range differs with the inner and outer diameters and other characteristics of a catheter body.

<Catheter Body with an Inner Diameter of at Least 800 μm and an Outer Diameter of at Least 950 μm>

(i) The yield force is not higher than 10.8 N, preferably not higher than 7.4 N, more preferably not higher than 6.4 N, further preferably not higher than 5.4 N, and most preferably not higher than 4.4 N.

(ii) The recovery force is not higher than 3.9 N, preferably not higher than 2.9 N, more preferably not higher than 2.0 N, and further preferably not higher than 1.0 N.

(iii) The residual strain is not smaller than 0.2 mm, preferably not smaller than 0.5 mm, more preferably not smaller than 0.9 mm, and further preferably not smaller than 1.2 mm.

<Catheter Body with an Inner Diameter of 600–800 μm and an Outer Diameter of 700–950 μm>

(i) The yield force is not higher than 8.8 N, preferably not higher than 6.4 N, more preferably not higher than 5.4 N, further preferably not higher than 4.4 N, and most preferably not higher than 2.9 N. The lowest limit is preferably not lower than 0.1 N though not particularly critical.

(ii) The recovery force is not higher than 2.9 N, preferably not higher than 1 N, and more preferably not higher than 0.5 N. The lowest limit is preferably 0 N though not particularly critical.

(iii) The residual strain is not smaller than 0.2 mm, preferably not smaller than 0.5 mm, more preferably not smaller than 0.9 mm, and further preferably not smaller than 1.2 mm. The upper limit is preferably not higher than 1.8 mm though not particularly critical.

<Catheter Body with an Inner Diameter of not Smaller than 250 μm to Less than 600 μm and an Outer Diameter of not Smaller than 350 μm to Less than 700 μm>

(i) The yield force is not higher than 6.9 N, preferably not higher than 4.9 N, more preferably not higher than 3.9 N, further preferably not higher than 2.9 N, and most preferably not higher than 2 N. The lowest limit is preferably not lower than 0.1 N though not critical.

(ii) The recovery force is not higher than 2 N, preferably not higher than 1 N, more preferably not higher than 0.5 N, and most preferably not higher than 0.1 N.

(iii) The residual strain is not smaller than 0.2 mm, preferably not smaller than 0.5 mm, more preferably not smaller than 0.9 mm, and further preferably not smaller than 1.2 mm.

<Catheter Body with an Inner Diameter of Less than 250 μm and an Outer Diameter of Less than 350 μm>

(i) The yield force is not higher than 2 N, preferably not higher than 1 N, and more preferably not higher than 0.9 N.

(ii) The recovery force is not higher than 1 N, preferably not higher than 0.6 N, and more preferably not higher than 0.1 N.

(iii) The residual strain is not smaller than 0.2 mm, preferably not smaller than 0.5 mm, more preferably not smaller than 0.9 mm, and further preferably not smaller than 1.2 mm.

If the yield force, recovery force and residual strain of a distal end portion (at least a portion extending 5 mm from the distal end, and especially a portion extending 30 cm from the distal end) of the catheter body in the three-point bending test are below the above ranges, the distal end portion of the catheter body is too flexible and the proximal end portion may become too low in rigidity or strength, sometimes giving rise to a problem in operation. On the other hand, if the yield force, recovery force and residual strain are beyond the above range, the distal end portion of the catheter body has a too strong restoring force, causing damage to the blood vessel or ureter, and the proximal end portion may become too high in rigidity or strength, sometimes giving rise to a problem in safety and operation.

It is noted that when a tubular member having an outer diameter of 875 μm and an inner diameter of 750 μm as the proximal end portion (a portion extending 5 mm from the proximal end) of the catheter body exhibits a yield force of not lower than 8.9 N, a recovery force of not lower than 3.0 N, and a residual strain of less than 0.2 mm as measured by a three-point bending test, this proximal end portion has sufficient rigidity. The yield force, recovery force and residual strain of an intermediate portion between the distal and proximal end portions of the catheter body can be suitably set in accordance with operation and other factors.

The catheter of the present invention essentially restores its original shape at least at the body temperature due to the shape memory effect, that is, the shape memory effect develops below the temperature at which the superelastic or pseudoelastic effect develops. In contrast, the catheter body in the form of a superelastic metal tube or shape memory alloy tube described in JP-A 3-188875 restores in less than 0.3 second after deformation and has a considerable yield force (that is, a large recovery force), and instantaneously restores the original shape due to the superelastic or pseudoelastic effect. The catheter body of the present invention utilizes only shape memory property and does not exert the superelastic or pseudoelastic effect that prior art catheters of this type possess.

In the practice of the invention, the tubular catheter body may be entirely formed of the said shape memory-specialized alloy. It is also preferable from the operating standpoint that only the distal end portion of the catheter body be formed of the shape memory-specialized alloy and the remaining parts formed of a shape memory alloy and the like having shape memory property at least at the body temperature as well as superelasticity or pseudoelasticity.

In this connection, it is recommended from the standpoint of more effectively achieving the object of the invention that the portion formed of the shape memory-specialized alloy is at least a portion of the catheter body which extends from the position of not less than 5 mm apart from the proximal end of the catheter body, preferably up to 10 cm, more preferably up to 20 cm, and further preferably up to 30 cm.

According to the invention, a Ni—Ti, Fe or Cu base shape memory alloy is heat or otherwise treated so that the catheter body may be formed of a shape memory-specialized alloy. Such shape memory alloys include Ni—Ti alloys, Ni—Ti—Co alloys, Ni—Ti—Fe alloys, Ni—Ti—Mn alloys, Ni—Ti—Cr alloys, Ni—Ti—V alloys, Ni—Ti—Al alloys, Ni—Ti—Nb alloys, Cu—Zn alloys, Cu—Zn—Be alloys, Cu—Zn—Si alloys, Cu—Zn—Sn alloys, Cu—Zn—Ga alloys, Cu—Al—Ni alloys, and Cu—Al—Zn alloys. There may be used an alloy whose alloy composition is changed in accordance with the application and the extent of shape memory effect. In particular, Ni—Ti alloys having a Ni concentration of 49 to 58 atomic %, preferably 50 to 51 atomic %, more preferably 50.3 to 50.7 atomic % are preferable.

The shape memory alloy tube of which the catheter body of the invention is constructed may be formed by customarily cold working a shape memory alloy tube of a predetermined diameter (for example, to a working ratio of 30 to 50%) and drawing in a conventional manner. Thereafter, heat treatment is preferably carried out at a temperature of 350 to 700° C. for 1 minute to several hours, especially 10 minutes to 1 hour although the heat treating conditions remain indefinite and vary with the type of shape memory alloy and in the case of an Ni—Ti alloy, its Ni concentration.

According to the invention, heat treatment is further carried out in an inert atmosphere of nitrogen gas or argon gas in order to convert the shape memory alloy (of at least the distal end portion) into a shape memory-specialized alloy in which the superelasticity or pseudoelasticity of the shape memory alloy is lost, with its shape memory property maintained. The conditions for the further heat treatment vary with the type of shape memory alloy and may be suitably selected. In the case of Ni—Ti alloys, for example, the conditions include at not lower than 350° C. and 1 minute to 100 hours, preferably at not lower than 450° C. and 10 minutes to 50 hours, more preferably at not lower than 450° C. and 1 to 30 hours, in an inert atmosphere of argon gas or the like, although the conditions differ with a particular Ni concentration. In some cases, a procedure of heating at not lower than 500° C. for 10 hours or longer in an inert atmosphere of argon gas or the like may be employed.

Figure 7:
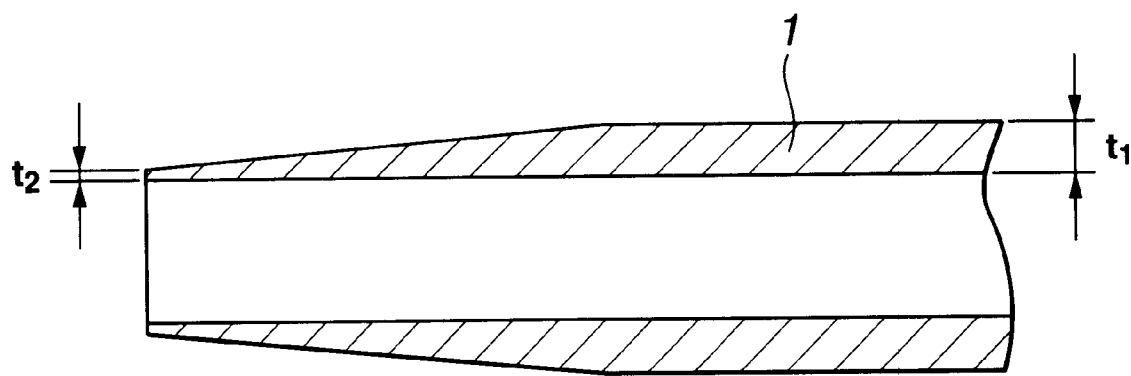
FIG. 7 is a cross-sectional view of a catheter body according to one embodiment of the invention.

The catheter of the present invention favors that the distal end portion of the catheter body which is formed of the shape memory-specialized alloy (and which extends at least about 30 cm from the distal end) is tapered as shown in FIG. 7. Tapering is effected under such conditions that in the catheter whose proximal end portion has a thickness t1 of 20 to 200 μm, preferably 30 to 100 μm, the distal end portion of the catheter has a thickness t2 of 5 to 100 μm, preferably 10 to 50 μm, and more preferably 20 to 40 μm. If too thin, the distal end portion may be longitudinally fissured. On the other hand, if the distal end portion is too thick, tapering the distal end portion may not function effectively. In this regard, the ratio of the distal end portion thickness t2 to the proximal end portion thickness t1 may be from ⅕ to ⅘, preferably from ¼ to ¾, and further preferably from ⅓ to ⅔. For example, t2 is preferably 25 to 30 μm when t1 is 50 μm.

By tapering the distal end portion of the catheter body, the distal end portion is endowed with flexibility so that the catheter can be smoothly introduced to the destination in a complex tortuous, sensitive blood vessel without damaging the blood vessel.

Figure 8:
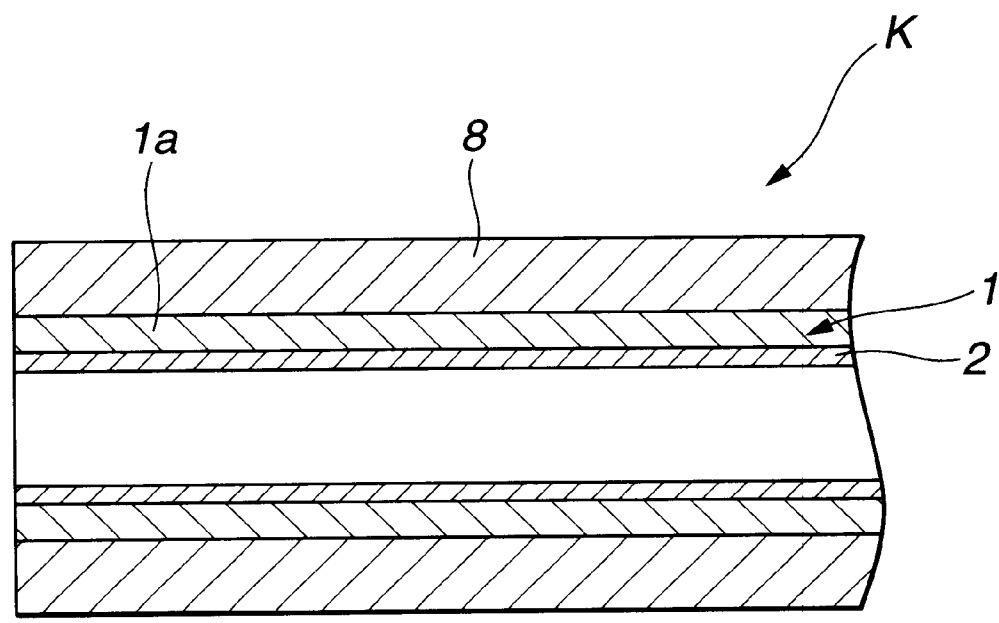
FIG. 8 is a cross-sectional view of the same catheter.

As seen from one exemplary construction shown in FIG. 8, the catheter K of the invention includes a catheter body whose distal end portion is made of the shape memory-specialized alloy and an outer polymer layer 8 covering the outer surface of the catheter body 1. If necessary, an inner polymer layer 2 may be formed on the inner surface of the catheter body 1. Further, on the outer polymer layer 8 (outermost layer) and the inner polymer layer 2 (innermost layer), a hydrophilic polymer such as polyurethane, nylon or polyolefin and the like may be coated for the purposes of increasing operability, and imparting durability, good anti-coagulant property, in-water lubrication and slime to the surface.

The materials of which the inner and outer polymer layers are made are not critical in the present invention and include polymers which withstand radiation or electron sterilization with electron beams or gamma-rays and so on as well as gas sterilization, for example, polyolefin polymers such as polyethylene, polypropylene, and polyolefin copolymers, polystyrene, polymethyl methacrylate, polyvinyl chloride, polyurethane, polyamide, polyester, fluoro-resins such as polytetrafluoroethylene, polycarbonate, silicone, cellulose, natural rubber latex, and other rubber.

The catheter body 1 may have a wall thickness of about 5 to 300 μm, and especially about 10 to 200 μm. The outer polymer layer 8 may have a thickness of 1 to 300 μm, preferably 20 to 300 μm, and especially 50 to 150 μm. The thickness of the inner polymer layer 2 is 10 to 100 μm when it is formed by internally inserting an inner polymer tube. The thickness of the inner polymer layer 2 is about 0.2 to 30 μm when it is formed by coating a thermoplastic resin polymer to the inner surface of the catheter body. The inner diameter of the catheter K may be suitably selected; specifically, the catheter can be formed as thin as 50 to 5,000 μm, and especially 100 to 1,000 μm in inner diameter.

It is noted that the thermoplastic resin of which the inner and outer polymer layers on the catheter are formed may contain an x-ray contrast medium. Any of well-known contrast mediums may be used herein. In the practice of the invention, tungsten powder is preferable. An appropriate content of the contrast medium is about 20 to 69% by weight, and preferably about 30 to 60% by weight.

The length of the catheter K may be suitably selected depending on an intended application.

Further, the distal end portion of the catheter can be shape memorized such that it may bend to a radius of curvature (R) of 0 to 200 mm at the body temperature. The distal end portion can also be shape memorized such that it may bend by an angle of 0 to 120 degrees, and especially 30 to 90 degrees at the body temperature. It is understood that a radius of curvature (R) of 0 mm indicates the straight state without bending, which is necessary in an application for a particular purpose. By shape memorizing the distal end portion of the catheter in this way, the catheter can be smoothly and easily introduced into a tortuous, sharply bent blood vessel or ureter.

It is noted that in the catheter of the present invention, a need for a leading guide wire can be eliminated by imparting strength or rigidity to the proximal side.

The catheter of the present invention can be used for the angiographic examination of the brain, heart, abdomen and so on, the treatment of blood vessel stricture in the brain, heart, abdomen and so on, the calculus-retrieving treatment of urinary tract system such as ureter and urethra, the examination of pancreatic and bile ducts, ERCP treatment, and the removal/recovery of foreign matter, in the same manner as conventional catheters. Specifically, in a customary way, the distal end of the catheter is inserted to the destination within the living body whereupon a medicament such as an angiocontrast medium or embolic substance is locally injected. Alternatively, an expandable/contractible balloon is attached to the distal end of the catheter whereby the catheter is used for the treatment of various blood vessels, ureter, and pancreatic and bile ducts.

There has been the first embodiment of the invention although the invention is not limited to the illustrated examples, and various changes may be made thereto insofar as the objects of the invention are achievable.

Second Embodiment of the Invention

The catheter according to the second embodiment of the invention is characterized by comprising a catheter body, an outer polymer layer covering the outer surface of the catheter body, and a thermoplastic resin tube joined to the distal end of the catheter body, and also by comprising a catheter body, a thermoplastic resin joined to the catheter body, and an outer polymer layer covering the outer surface from the distal end of the catheter body to at least the proximal side of the said thermoplastic resin tube and the whole catheter body itself, wherein in a region extending from the distal end portion of the catheter body to at least a proximal end portion of the thermoplastic resin tube, especially the joint between the catheter body and the thermoplastic resin tube and the vicinity thereof, a reinforcement is formed by winding in a coil fashion and/or braiding in a mesh fashion a linear elastic material selected from among a metal wire, organic wire and inorganic wire, or by attaching the linear elastic material on the surface along the axial direction, or any combination of the above. The catheter eliminates any step-like structure at the junction between the leading tube made of thermoplastic resin and the catheter body, minimizes the induction of unusual feeling and pain, and prevents the blood vessel from being damaged during operation as much as possible.

The catheter body used herein may be formed using any of tubes of flexible resins such as polystyrene, polyolefin, polyester, and polyurethane, and metallic tubes of stainless steel and shape memory alloys, which are conventionally used to form catheter bodies. For achieving the objects and benefits of the invention to the maximum extent, it is preferred that at least a distal end portion of the catheter body be formed of a shape memory-specialized alloy having shape memory property, but free from superelasticity or pseudoelasticity at least at the body temperature (typically about 33 to 42° C., and preferably in the range of 35 to 38° C.), as in the first embodiment.

It is preferred herein that when at least the distal end portion of the catheter body is deformed at the body temperature, restoration takes not less than 0.3 second. Also, at least the distal end portion of the catheter body is preferably formed of a metal material which exhibits a yield force of not higher than 8.8 N, a recovery force of not higher than 2.9 N, and a residual strain of not lower than 0.2 mm when a three-point bending test is carried out on a metal tube having an outer diameter of 875 μm and an inner diameter of 750 μm. Notably, the preferred range of the results of the catheter body in the three-point bending test is the same as in the first embodiment.

The method of joining the thermoplastic resin tube to the catheter body includes (i) a method of bonding the thermoplastic resin tube directly to the distal end of the catheter body and (ii) a method of joining the thermoplastic resin tube to the catheter body through the inner polymer layer formed on the inner surface of the catheter body.

In the joining method (i), the distal end of the catheter body is bonded to the proximal end of the thermoplastic resin tube, and in a region extending from the distal end portion of the catheter body to at least a proximal end portion of the thermoplastic resin tube, especially the joint there between and the vicinity thereof, a linear elastic material selected from among a metal wire, organic wire and inorganic wire is wound in a coil fashion and/or braided in a mesh fashion, or is attached on the surface along the axial direction, or is used in any combination of methods described above to form a reinforcement.

In the joining method (ii), an inner polymer tube is inserted into the catheter body to form an inner polymer layer on the inner surface of the catheter body whereby the inner polymer layer joins the thermoplastic resin tube to the distal end of the catheter body, and in a region extending from the distal end portion of the catheter body to at least a proximal end portion of the thermoplastic resin tube, especially the joint there between and the vicinity thereof, a linear elastic material selected from among a metal wire, organic wire and inorganic wire is wound in a coil fashion and/or braided in a mesh fashion, or is attached on the surface along the axial direction, or is used in any combination of methods described above to form a reinforcement.

In the above joining methods (i) and (ii), it is preferred that not only in the joint between the catheter body and the thermoplastic resin tube and the vicinity thereof, but also in a region from the joint to the distal end of the thermoplastic resin tube, a linear elastic material selected from among a metal wire, organic wire and inorganic wire is wound in a coil fashion and/or braided in a mesh fashion, or is attached on the surface along the axial direction, or is used in any combination of methods described above to form a reinforcement. Further, a region from the proximal end portion to the distal end portion of the catheter body can be reinforced by similar coil winding and/or mesh braiding or combination thereof.

The above joining method (i) merely requires to polish the inner surface of the catheter body since the thermoplastic resin tube is joined directly to the distal end of the catheter without utilizing the inner polymer layer. Alternatively, it suffices that the inner surface is coated with a thermoplastic resin polymer such as polyurethane, nylon or polyolefin to form an inner polymer layer. Thus the joining method (i) is highly advantageous for manufacturing. Herein, the inner polymer layer may be formed on the inner surface extending from the catheter body to the distal end of the thermoplastic resin tube. It is noted that an anti-coagulant hydrophilic polymer is preferably coated on the inner polymer layer (innermost layer).

The method of forming the reinforcement in a region extending from the distal end portion of the catheter body to at least the proximal end portion of the thermoplastic resin tube, especially the joint between the catheter body and the thermoplastic resin tube and the vicinity thereof, includes (a) external winding of a linear elastic material in a coil fashion and/or external braiding in a mesh fashion, or attaching this linear elastic material along the axial direction, or any combination thereof and (b) internal winding of linear elastic material in a coil fashion and/or internal braiding in a mesh fashion, or attaching this linear elastic material along the axial direction, or any combination thereof.

The above method (a) is illustrated, for example, in FIGS. 9(A) to 9(C) through FIGS. 11(A) to 11(D). In these cases, the catheter body can be coated with an adhesive polymer to improve the tight binding.

Figure 9A:
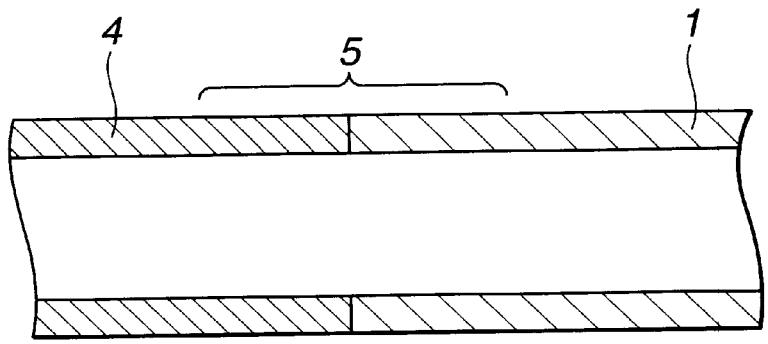
FIGS. 9(A) to (C) are cross-sectional views showing a method of joining a thermoplastic resin tube to the distal end of a catheter body of the present invention and forming a reinforcement.
Figure 9B:
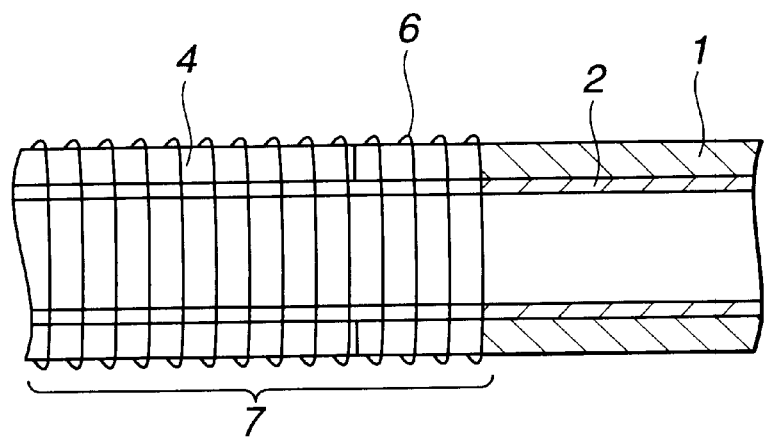
Figure 9C:
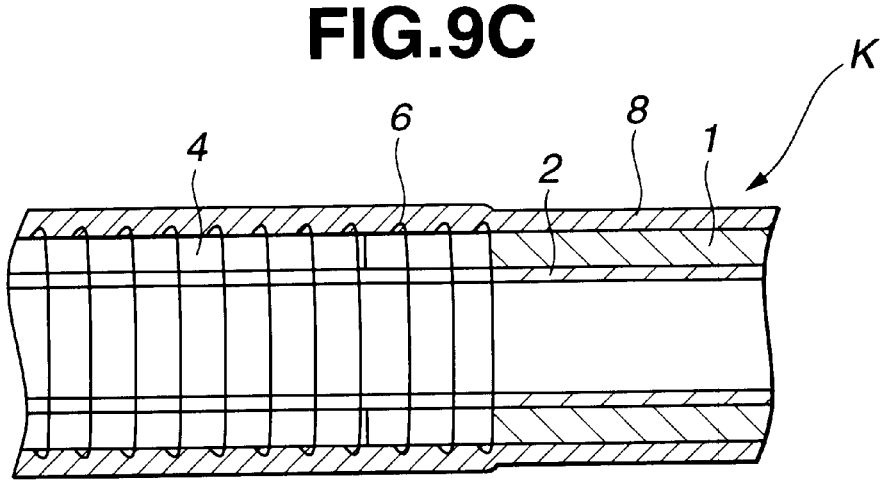

More particularly, as shown in FIG. 9(A), the proximal end of a thermoplastic resin tube 4 is bonded to the distal end of a tubular catheter body 1. Then a linear elastic material 6 selected from among a metal wire, organic wire and inorganic wire is wound around the joint between the thermoplastic resin tube and the catheter body and the vicinity 5 thereof in a coil fashion to form a reinforcement 7 as shown in FIG. 9(B). In this state, an outer polymer layer 8 is formed by coating on the outer surface of the catheter body 1 and the thermoplastic resin tube 4, resulting in a catheter K as shown in FIG. 9(C). It is noted that on the inner surface extending from the catheter body to the thermoplastic resin tube is coated with a thermoplastic resin polymer such as polyurethane, nylon or polyolefin to form an inner polymer layer 2.

Figure 10A:
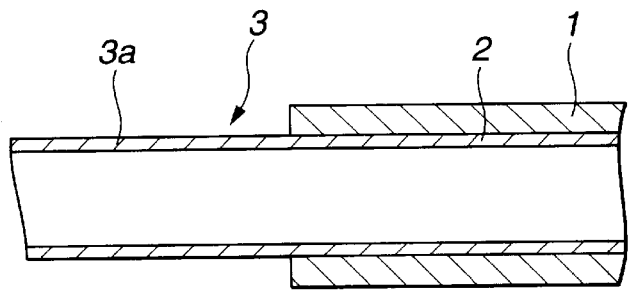
FIGS. 10(A) to (D) are cross-sectional views showing a method of joining a thermoplastic resin tube to the distal end of the same catheter body and forming a reinforcement.
Figure 10B:
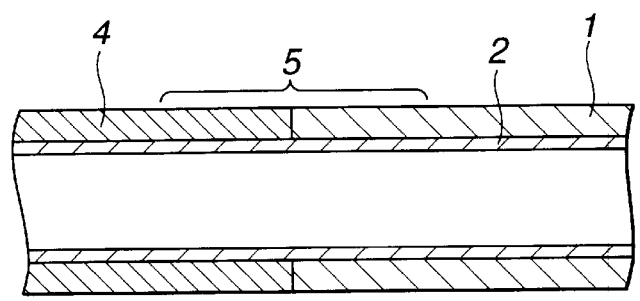
Figure 10C:
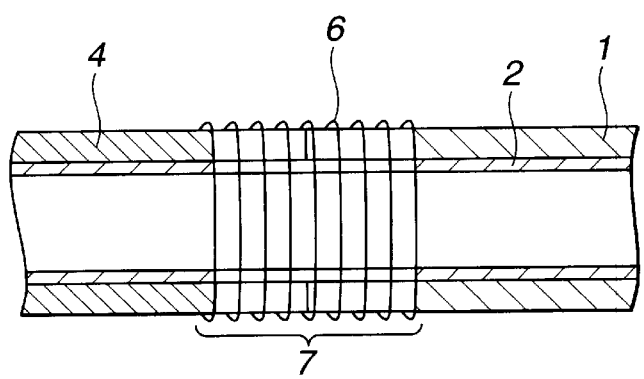
Figure 10D:
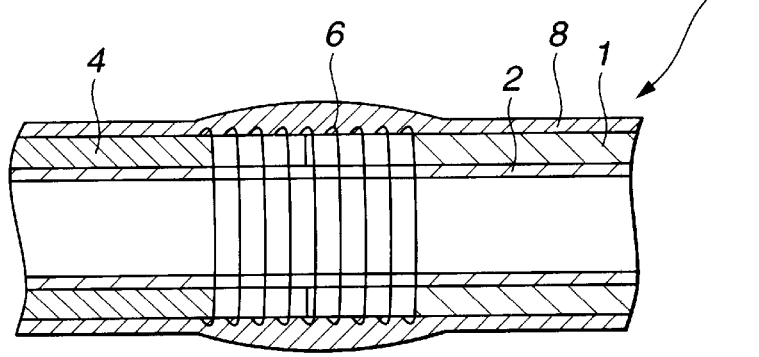

Also as shown in FIG. 10(A), an inner polymer tube 3 is inserted into a tubular catheter body 1 such that the inner polymer tube 3 may project beyond the distal end of the catheter body 1, whereby an inner polymer layer 2 is formed on the inner surface of the catheter body 1. A thermoplastic resin tube 4 is fitted over the projection 3a of the inner polymer tube and the proximal end of the thermoplastic resin tube is bonded to the distal end of the catheter body as shown in FIG. 10(B). Then a linear elastic material 6 selected from among a metal wire, organic wire and inorganic wire is wound around the joint between the thermoplastic resin tube and the catheter body and the vicinity 5 thereof in a coil fashion to form a reinforcement 7 as shown in FIG. 10(C). In this state, an outer polymer layer 8 is formed by coating on the outer surface of the catheter body 1 and the thermoplastic resin tube 4, resulting in a catheter K as shown in FIG. 10(D).

Figure 11A:
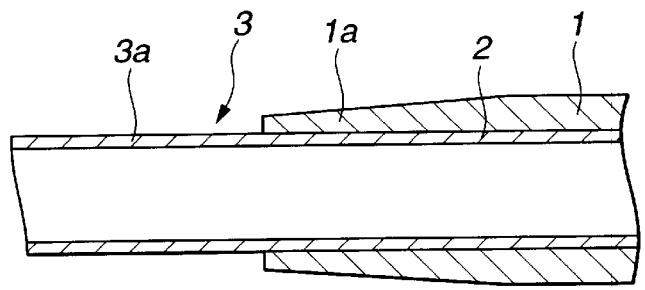
FIGS. 11(A) to (D) are cross-sectional views wherein a distal end portion of the catheter body and a proximal end portion of the thermoplastic resin tube are tapered.
Figure 11B:
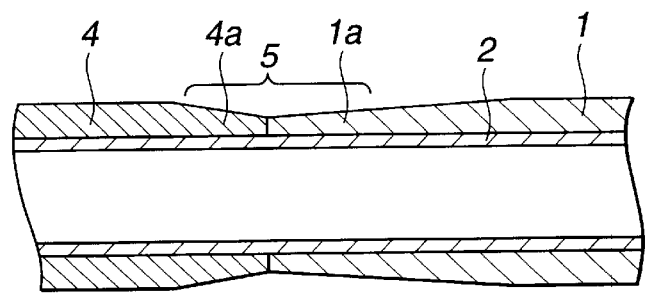
Figure 11C:
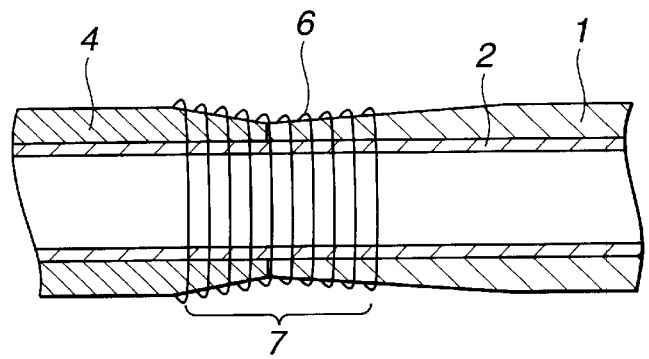
Figure 11D:
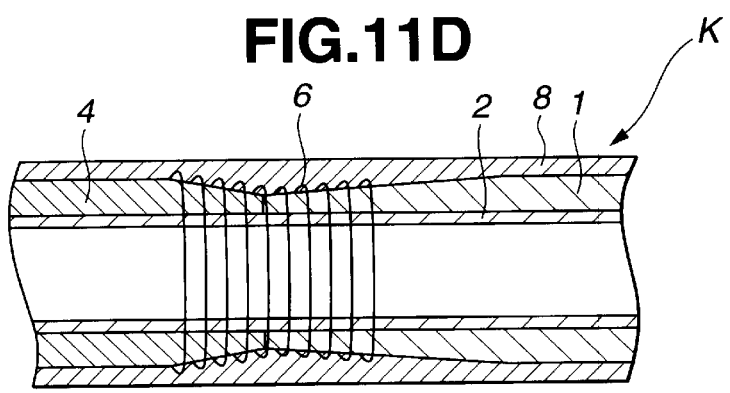

An alternative embodiment is shown in FIGS. 11(A) to 11(D). Where the distal end portion 1a of the catheter body is tapered as shown in FIG. 7, a proximal end portion 4a of a thermoplastic resin tube 4 is also tapered in conformity with the catheter body. A linear elastic material 6 selected from among a metal wire, organic wire and inorganic wire is wound around the joint between the tapered portions and the vicinity 5 thereof in a coil fashion to form a reinforcement 7 as shown in FIG. 11(C). In this state, an outer polymer layer 8 is formed by coating on the outer surface of the catheter body 1 and the thermoplastic resin tube 4, resulting in a catheter K as shown in FIG. 11(D). The method of FIG. 11 is advantageous in that any buildup is eliminated from the joint and the vicinity so that the diameter of the catheter may be formed uniform and small.

Figure 12A:
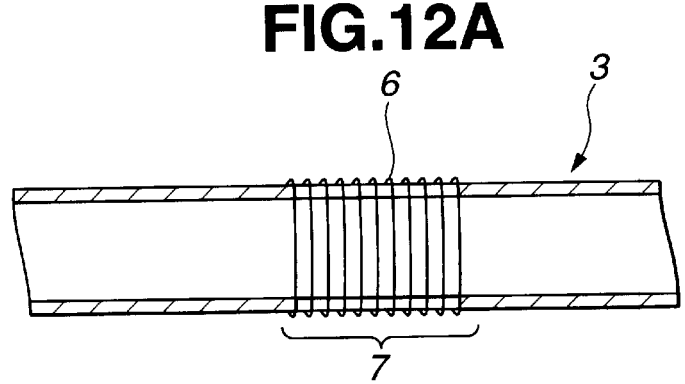
FIGS. 12(A) to (D) are cross-sectional views wherein the reinforcement is formed by internal winding.
Figure 12B:
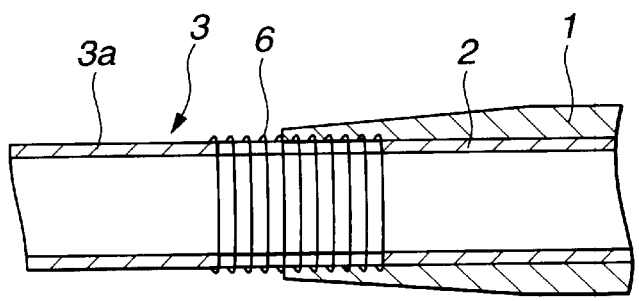
Figure 12C:
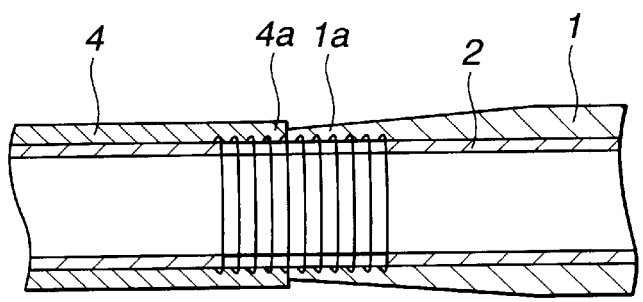
Figure 12D:
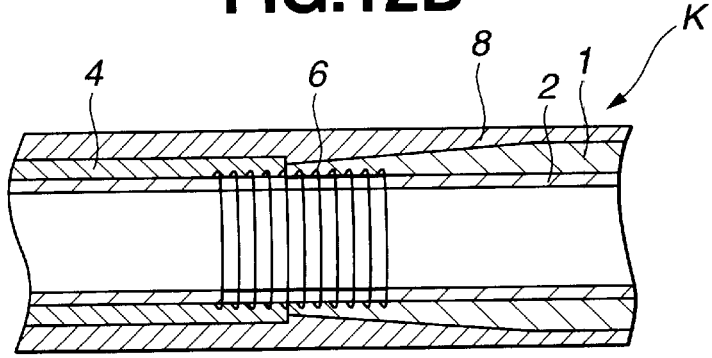

In the above method (b) on the other hand, as shown in FIGS. 12(A) to 12(D), a linear elastic material 6 selected from among a metal wire, organic wire and inorganic wire is wound around a region of an inner polymer tube 3 where it is to be joined to a catheter body and the vicinity thereof in a coil fashion to form a reinforcement 7 as shown in FIG. 12(A). This inner polymer tube 3 is inserted into a tubular catheter body 1 such that about one half of the reinforcement 7 may project beyond the tubular catheter body 1, whereby an inner polymer layer 2 is formed on the inner surface of the catheter body 1 as shown in FIG. 12(B). A thermoplastic resin tube 4 is fitted over the projected portion 3a, and the proximal end 4a of the thermoplastic resin tube is bonded to the distal end 1a of the catheter body as shown in FIG. 12(C). In this state, an outer polymer layer 8 is formed by coating on the outer surface of the catheter body and the thermoplastic resin tube, resulting in a catheter K as shown in FIG. 12(D). It is also preferred in this embodiment of method (b) that the distal end portion of the catheter body and the proximal end portion of the thermoplastic resin tube be tapered.

Though not shown, it is also possible that by combining the above methods (a) and (b) together, reinforcements are formed on both the inside and outside of the joint between the catheter body and the thermoplastic resin tube and the vicinity thereof. Further, the above embodiments illustrate the coil winding form of reinforcement only although a reinforcement can, of course, be formed by mesh braiding or by attaching a linear elastic material along the axial direction, or by any combination of the above.

In this case, by attaching a linear elastic material along the axial direction, not only reinforcement of the joint region and the vicinity thereof between the catheter body and the thermoplastic resin, but also prevention of the extension of the catheter in the axial direction can be achieved, which improves the operability further. The methods for attaching such linear elastic material along the axial direction is not limited particularly, and methods by attaching with adhesives, thermal-bonding, embedding in the inner or outer polymer layers, and so on, can be employed. Also, one to 10 pieces, preferably 2 to 6 pieces of the linear elastic material is preferably attached along the axial direction uniformly.

The linear elastic material selected from among a metal wire, organic wire and inorganic wire to form the reinforcement includes metal wires such as platinum coil, stainless steel coil, and tungsten coil, and filaments of various thermoplastic elastomers such as polystyrene, polyolefin, polyester and polyurethane, with filaments of nylon 6, aromatic polyesters (trade name Vectoran by Kurare K.K.), and aramid (trade name Kevlar by Dupont) being especially preferred. Also, fibrous proteins such as collagen extracted from bovine tendon, carbon fibers, glass fibers, and other inorganic wires are useful.

The width of the coil or mesh (that is, the length of the reinforcement) is not critical as long as the joint between the catheter body and the thermoplastic resin tube and the vicinity thereof can be sufficiently wrapped. More preferably, coil winding and/or mesh braiding is effected not only on the joint and the vicinity thereof, but also on the region extending from the joint to the distal end of the thermoplastic resin tube, to form the reinforcement. It is noted that a reinforcement can also be formed by effecting coil winding and/or mesh braiding on the region extending from the proximal end portion of the catheter body to the joint and further to the distal end of the thermoplastic resin tube.

The material of which the thermoplastic resin tube is constructed is not critical, and the same materials as the inner and outer polymer layers in the first embodiment may be used. The length of the thermoplastic resin tube is not critical although it is preferably about 1 mm to 200 cm, preferably about 1 mm to 50 cm, and more preferably about 1 mm to about 30 cm long.

Now that a reinforcement is formed on the joint between the thermoplastic resin tube and the catheter body distal end and the vicinity thereof by winding in a coil fashion and/or braiding in a mesh fashion of a linear elastic material selected from among a metal wire, organic wire and inorganic wire, the distal end portion of the catheter is endowed with improved flexibility so that the catheter can be smoothly introduced into a complex tortuous thin blood vessel, ureter, pancreatic duct or bile duct without folding whereby the cause of unusual feeling and pain is prevented as much as possible.

In the present invention, it is possible to form a nickel-free metal layer (inner metal layer) between the inner surface of at least the shape memory-specialized alloy portion of the catheter body and the inner polymer layer and/or a metal layer (outer metal layer) between the outer surface of the catheter body and the outer polymer layer.

Figure 13:
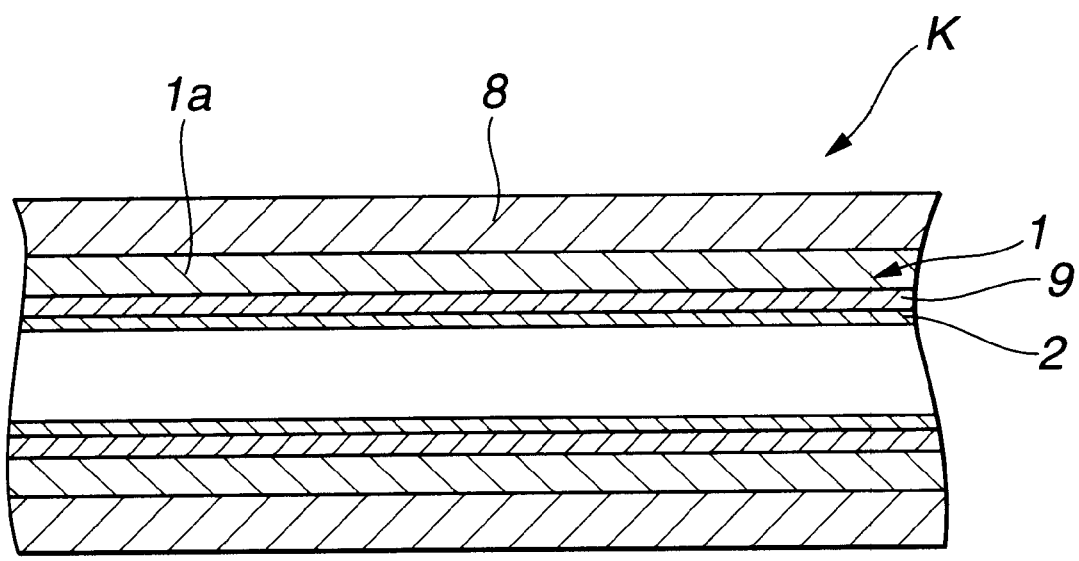
FIG. 13 is a cross-sectional view of a catheter according to one embodiment of the invention.

FIG. 13 is a cross-sectional view of a distal end portion of a catheter K according to such an embodiment. It is understood that a thermoplastic resin tube is joined to the distal end of the catheter K though not shown. The catheter K includes an outer polymer layer 8 enclosing the outer surface of a catheter body 1 whose distal end portion is made of the shape memory-specialized alloy 1a and an inner nickel-free metal layer 9 between the inner surface of the catheter body 1 and the inner polymer layer 2. It is possible to form an outer metal layer between the outer surface of the catheter body 1 and the outer polymer layer 8 though not shown. Further, on the outer polymer layer 8 (outermost layer) and the inner polymer layer 2 (innermost layer), a hydrophilic polymer such as polyurethane, nylon or polyolefin may be coated for the purposes of increasing operability, and imparting durability, good anti-coagulant property, in-water lubrication and slime to the surface.

The resins of which the inner and outer polymer layers 2 and 8 are formed may be the same thermoplastic resin as used in the above-described thermoplastic resin tube.

For the inner metal layer 9 of nickel-free metal, use is preferably made of high conductivity metals, for example, copper, silver, gold, platinum, palladium, tungsten, tantalum, iridium and alloys thereof. The outer metal layer formed between the outer surface of the catheter body 1 and the outer polymer layer 8 may contain nickel and be formed of the same materials as the above-described inner metal layer 9.

When the shape memory-specialized alloy portion is of Ni—Ti alloy, release of nickel ions into the living body is prevented by forming a polymer layer or an inner nickel-free metal layer over the inner surface of the shape memory-specialized alloy portion.

Also, when a high conductivity metal layer is formed on the inner surface of the catheter body or on the inner and outer surfaces of the catheter body, this metal layer is effective not only for the protection of the inner and outer surfaces, but also for fusion tearing-off of the thermoplastic resin tube, release of a connector for a medical wire having an in vivo implanting component, and release of a connecting polymer such as PVA or EVA for bonding an in vivo implanting component.

In this case, a variety of electrically released in vivo implanting components can be readily and reliably cut off. For example, when an in vivo implanting component is injected into a catheter whose inner surface is formed of a nickel-free metal and passed past the position of a connector (of PVA etc.), monopolar high-frequency current is conducted through the catheter to effect melt tearing-off of the thermoplastic resin tube.

For the patient to whom the use of high-frequency current is inadequate, an outer metal layer is formed on the outer surface of the catheter body so that bipolar high-frequency current may be supplied using the inner metal layer on the inner surface of the catheter body and the outer metal layer on the outer surface thereof whereby the thermoplastic resin tube can be melt torn off. The catheter of the present invention is also applicable to brain wave measurement.

The thickness of the catheter body 1, outer polymer layer 8 and inner polymer layer 2 and the inner diameter of the catheter are the same as in the first embodiment. The inner metal layer 9 may have a thickness of 0.2 to 20 $\mu$m and the outer metal layer have a thickness of 0.2 to 20 $\mu$m.

In manufacturing the catheter having metal layers formed on the inner and outer surfaces of the catheter body, a metal coating is formed on the inner and outer surfaces of a shape memory alloy tube of a predetermined diameter, by a suitable technique such as electroplating or electroless plating, especially electroless plating, and the tube is then drawn by a conventional technique.

The catheter of the present invention having a hydrophilic polymer coated on its innermost and outermost surfaces is improved in anti-coagulant property and surface slide and possesses all the factors necessary for clinical operation. The present invention is applicable to a wide variety of catheters ranging from those with a large diameter to those with a very small diameter and can be smoothly and reliably inserted to the destination through a tortuous thin blood vessel or ureter in the heart, brain, abdomen or urinary tract, without causing damage to the blood vessel or ureter.

There has been the second embodiment of the invention although the invention is not limited to the illustrated examples, and various changes may be made thereto insofar as the objects of the invention are achievable.

Third Embodiment of the Invention

The third embodiment of the invention provides a catheter comprising a catheter body and an outer polymer layer covering the outer surface of the catheter body, characterized in that the outer polymer layer is projected forward, and the catheter body is provided at a distal end with an injection part having lumen perforated therein, wherein the forward projection of the outer polymer layer can be radially dilated by injecting an injection fluid selected from saline, an embolic material and a contrast medium and the like through the lumen into the interface or space between the injection part and the forward projection of the outer polymer layer to fill the interface or space therewith. The catheter ensures to block blood or fluid flow at the destination and allows for angiography of a blood vessel or ureter and embolization of lesion in a safe and reliable manner while maintaining the blocked state of the blood flow.

The catheter body used herein may be formed using any of tubes of flexible resins such as polystyrene, polyolefin, polyester, and polyurethane, and metallic tubes of stainless steel and shape memory alloys, which are conventionally used to form catheter bodies. For achieving the objects and benefits of the invention to the maximum extent, it is preferred that at least a distal end portion of the catheter body be formed of a shape memory-specialized alloy having shape memory property, but free from superelasticity or pseudoelasticity at least at the body temperature (typically about 33 to 42° C., and preferably in the range of 35 to 38° C.), as in the first embodiment.

It is preferred herein that when at least the distal end portion of the catheter body is deformed at the body temperature, restoration takes not less than 0.3 second. Also, at least the distal end portion of the catheter body is preferably formed of a metal material which exhibits a yield force of not more than 8.8 N, a recovery force of not more than 2.9 N, and a residual strain of not less than 0.2 mm when a three-point bending test is carried out on a metal tube having an outer diameter of 875 $\mu$m and an inner diameter of 750 $\mu$m. Notably, the preferred range of the results of the catheter body in the three-point bending test is the same as in the first embodiment.

Figure 14A:
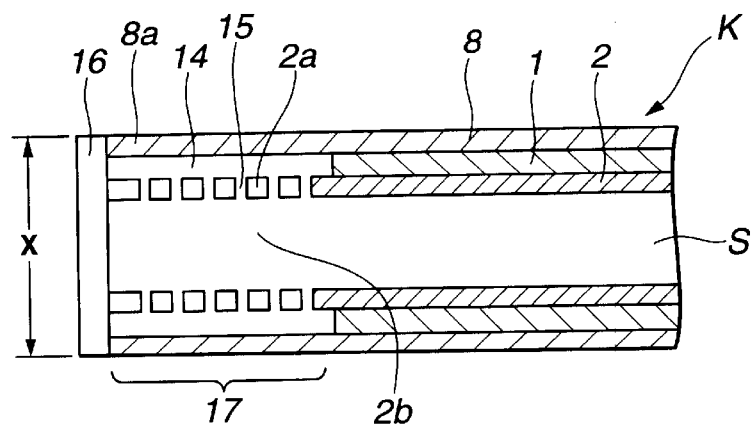
FIGS. 14(A) to (C) are fragmentary cross-sectional views of a catheter having a space defined in a distal end portion according to a first example of the invention.
Figure 14B:
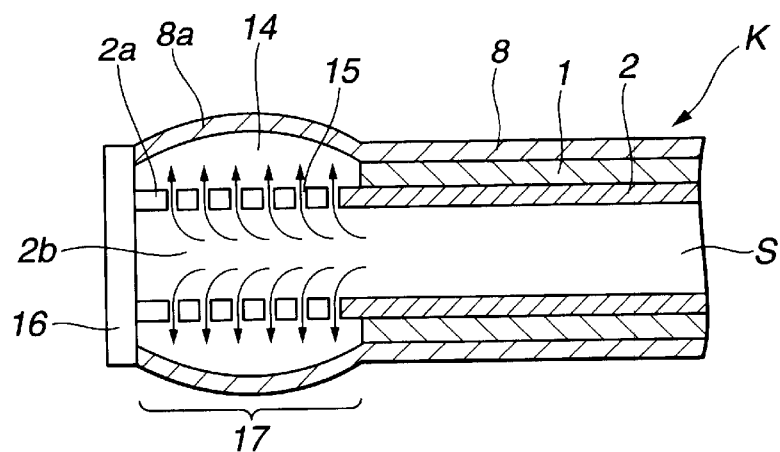
Figure 14C:
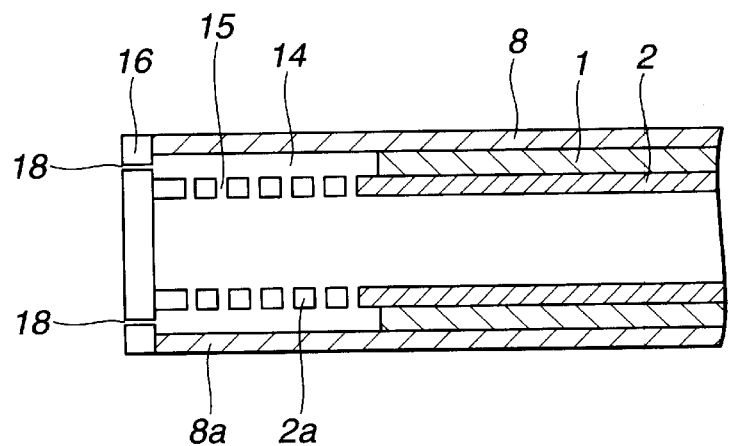

FIGS. 14(A) to 14(C) illustrate a first example of the invention. In a catheter K having a catheter body 1 and two inner and outer polymer layers 2 and 8 covering the inner and outer surfaces of the catheter body 1, the two inner and outer polymer layers 2 and 8 are projected forward as an injection part. An annular space 14 is defined between the forward projection 2a of the inner polymer layer 2 and the forward projection 8a of the outer polymer layer 8, and a number of lumina 15 is formed in the forward projection 2a of the inner polymer layer 2 for providing fluid communication between the space 14 and a hollow portion 2b of the inner polymer layer constructing a distal portion of a catheter lumen S.

In this example, distal openings of the hollow portion 2b of the inner polymer layer and the annular space 14 may be left open although it is preferred for more effective radial dilation of the forward projection 8a of the outer polymer layer 8 that a lid 16 made of a thermoplastic resin and the like is provided for closing distal openings of the hollow portion 2b of the inner polymer layer and the annular space 14 as shown in FIG. 14.

In the catheter shown in FIG. 14, an injection fluid such as saline, an embolic material or a contrast medium is injected into the catheter lumen S whereupon the injection fluid passes through the lumen 15 to fill the space 14 whereby the distal end portion 17 (specifically, the forward projection 8a of the outer polymer layer 8) of the catheter is outwardly or radially dilated as shown in FIG. 14(B).

In this example, the catheter distal end portion 17 (specifically, the forward projection 8a of the outer polymer layer 8) is dilated to such an extent as to moderately oppress the target blood vessel and the like for blocking the blood flow and the like thereacross. Provided that the catheter distal end portion 17 normally has an outer diameter of X mm, the dilated distal end portion has a maximum diameter of 1.1× to 5.0×, preferably 1.2× to 3.0×, more preferably 1.2× to 2.0×, and further preferably 1.2× to 1.7×.

Also in the catheter K of the invention, in order that the injection fluid such as saline, an embolic material or a contrast medium is discharged outside while the catheter distal end portion 17 (specifically, the forward projection 8a of the outer polymer layer 8) is being dilated therewith, the lid 16 is preferably provided with discharge lumen 18 for communicating the space 14 with the outside as shown in FIG. 14(C). The number of discharge lumen is generally about 1 to about 20.

Figure 15:
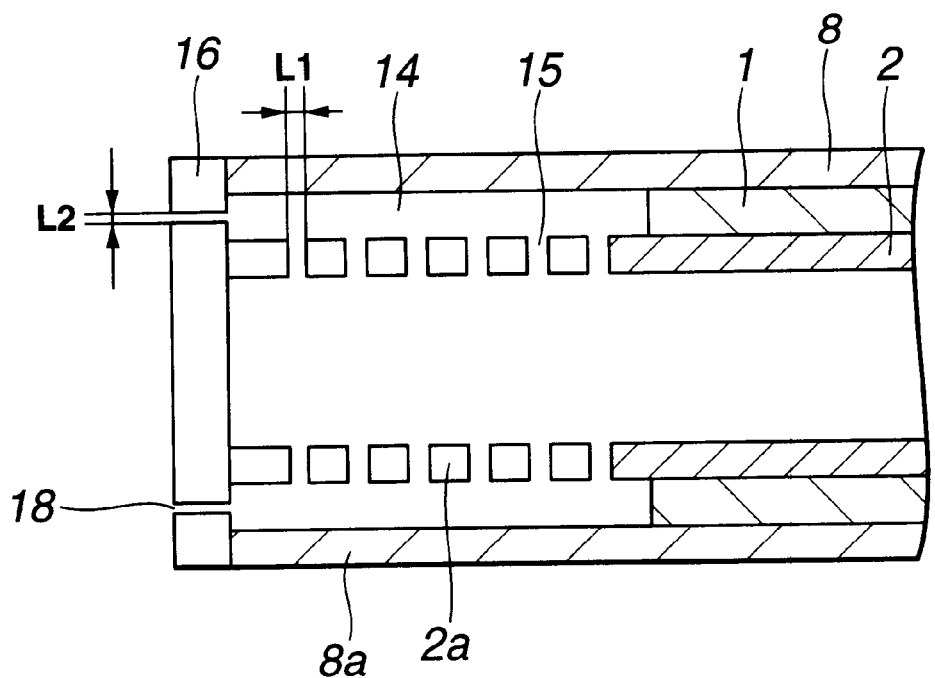
FIG. 15 is an enlarged fragmentary cross-sectional view of the same catheter.

The length of the catheter distal end portion 17 (specifically the length of the space 14) is not critical although it is usually about 1 to 100 mm, preferably 5 to 50 mm long. The diameter L1 and the number of lumen 15 perforated in the forward projection 2a of the inner polymer layer 2 are suitably adjusted for a particular application although the diameter L1 is usually about 10 to 200 $\mu$m and the number of lumen is usually 1 to 100, preferably 2 to 50 (see FIG. 15). Preferably the lumen are evenly distributed.

Figure 16:
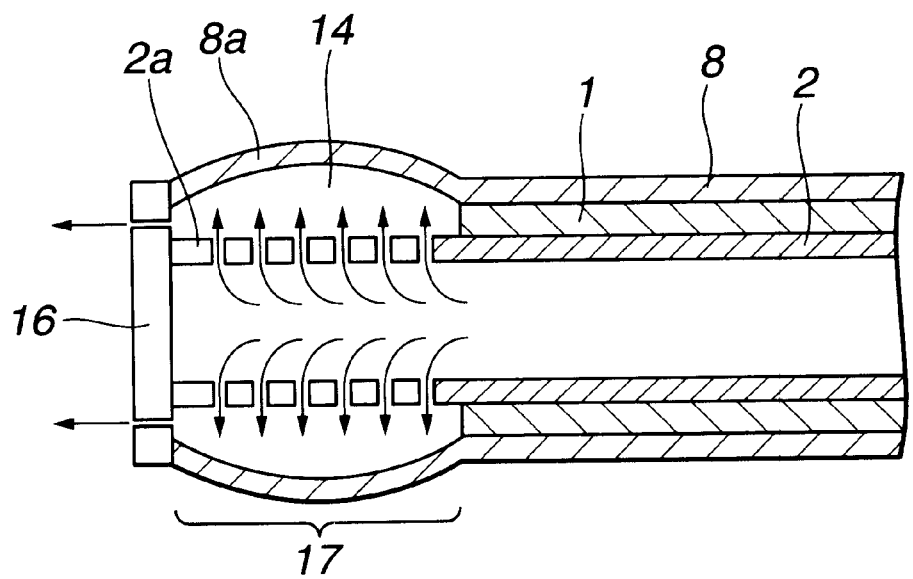
FIG. 16 is a fragmentary cross-sectional view of the same catheter whose distal end portion is dilated.

Often, the discharge lumen 18 preferably have an inner diameter L2 of about 10 to 200 $\mu$m. With this setting, while the catheter distal end portion 17 (specifically, the forward projection 8a of the outer polymer layer 8) is kept dilated for blocking the blood or fluid flow, the injection fluid such as saline, an embolic material or a contrast medium can be discharged outside through the discharge lumen 18 perforated in the catheter distal end (or lid 16) as shown in FIG. 16.

The thermoplastic resins of which the inner and outer polymer layers are formed are not critical and may be the same as in the above-described first and second embodiments. The thickness of the catheter body 1, the thickness of the outer polymer layer 8, the thickness of the inner polymer layer 2, and the inner diameter of the catheter may be the same as in the first and second embodiments.

Figure 17A:
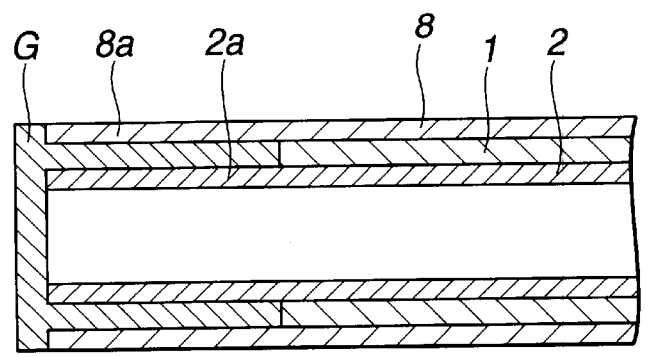
FIG. 17(A) being a cross-sectional view showing the catheter with a guide attached to the distal end thereof.
Figure 17B:
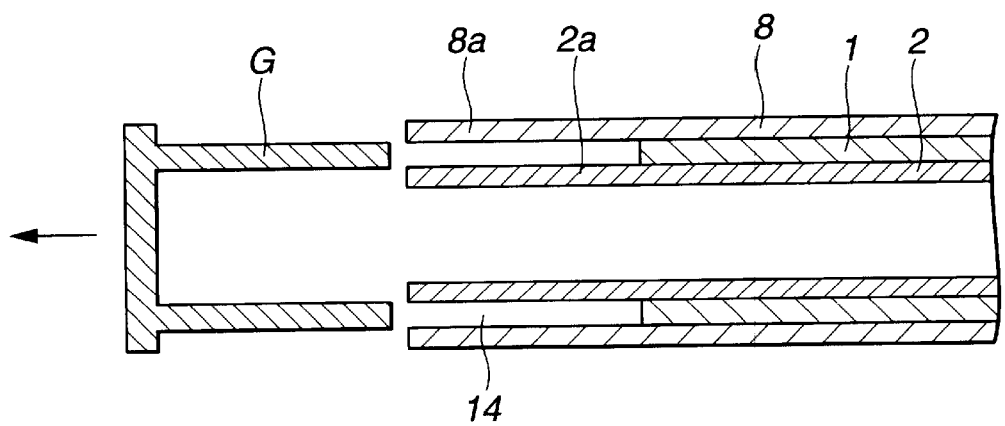
FIG. 17(B) being a cross-sectional view showing the catheter with the guide detached.
Figure 17C:
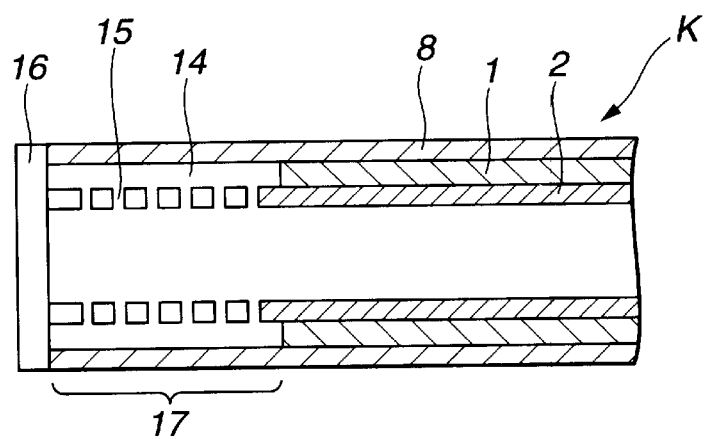
FIG. 17(C) being a cross-sectional view showing the catheter with a space defined in a distal end portion thereof.

The catheter having a space defined in its distal end portion according to the invention can be fabricated, for example, by the method illustrated in FIGS. 17(A) to 17(C). More particularly, a metallic guide G having an annular protrusion corresponding to the dimensions of the space is previously attached to the distal end of a catheter body 1. In this state, an inner polymer layer 2 and an outer polymer layer 8 are formed by coating on the inner and outer surfaces of the metallic guide G and catheter body 1, respectively, as shown in FIG. 17(A). Then the guide G is withdrawn in the direction of an arrow as shown in FIG. 17(B). The inner polymer layer 2 is perforated to define lumen 15 as shown in FIG. 17(C). The distal end of the catheter is closed with a lid 16. There is obtained the catheter K having the space 14 defined in its distal end portion 17 (specifically, the forward projection 8a of the outer polymer layer 8). Understandably, the lid 16 can be formed with discharge lumen (not shown) if necessary.

The method for fabricating the catheter of this embodiment is not limited to the above. Though not shown, the catheter can be fabricated by previously perforating an inner polymer layer (tube) to define lumen in its distal end portion, inserting the tube into the catheter body such that the distal end portion may project forward, and then forming an outer polymer layer optionally using a metallic guide as mentioned above.

Figure 18A:
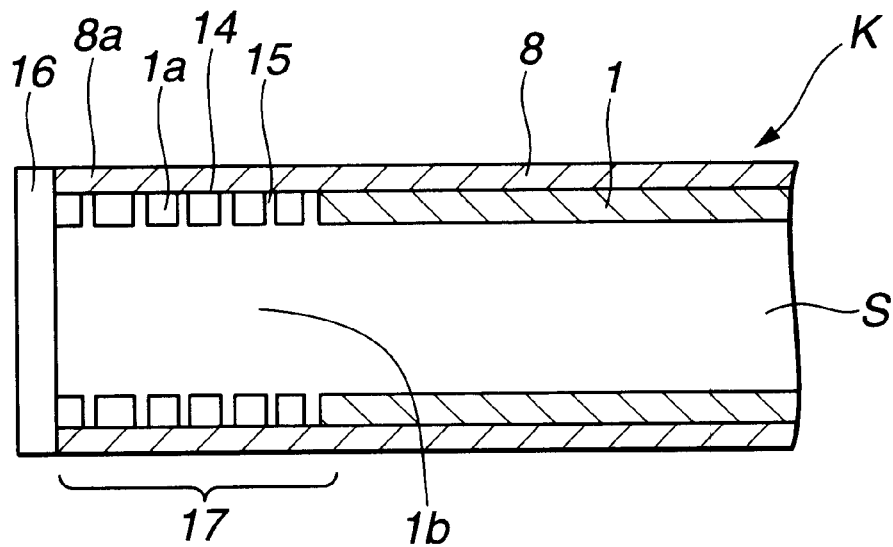
FIGS. 18(A) and (B) illustrate a catheter according to a second example of the invention, FIG. 18(B) being a fragmentary cross-sectional view showing the catheter whose distal end portion is dilated.
Figure 18B:
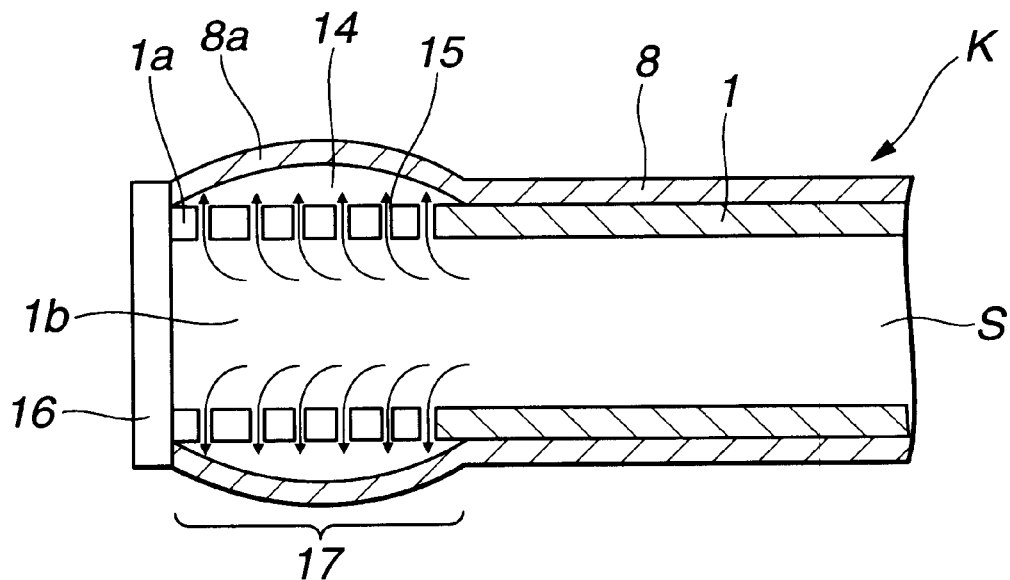

FIGS. 18(A) and 18(B) illustrate a catheter according to a second example. In this catheter K, the injection part is constructed by projecting forward the catheter body 1 and the outer polymer layer 8 such that the forward projection 1*a* of the catheter body 1 may be spaced apart at 14 from the forward projection 8*a* of the outer polymer layer 8, and perforating lumen 15 in the forward projection 1*a* of the catheter body 1. The interface or gap 14 between the forward projections 1*a* and 8*a* is in communication with a hollow portion 1*b* constructing a distal portion of a catheter lumen S. The remaining constructions are the same as in the first example. It is noted that instead of the forward projection 1*a* of the catheter body, a plastic tube perforated with lumen may be attached to the distal end of the catheter body to construct the injection part.

This example merely requires to polish the inner surface of the catheter body (herein, the formation of the inner polymer layer may be omitted). Alternatively, the inner surface of the catheter body (excluding the forward projection) is coated with a thermoplastic resin polymer such as polyurethane, nylon or polyolefin to form an inner polymer layer of 0.2 to 30 μm thick. It is noted that an anti-coagulant hydrophilic polymer is preferably coated on the inner polymer layer (innermost layer).

In the catheter shown in FIG. 18, an injection fluid such as saline, an embolic material or a contrast medium is injected into the catheter lumen S whereupon the injection fluid passes through the lumen 15 to fill the gap 14 between the forward projection 1*a* of the catheter body and the forward projection 8*a* of the outer polymer layer whereby the distal end portion 17 (specifically, the forward projection 8*a* of the outer polymer layer 8) of the catheter is outwardly dilated as shown in FIG. 18(B). Though not shown, in the catheter of the second example, of course, the lid 16 may be provided with discharge lumen so that the injection fluid such as an embolic material can be discharged through the discharge lumen while the distal end portion is kept dilated.

The method for fabricating the catheter of the second example is not critical. For example, a forward projection of a catheter body is perforated with lumen near the distal end, a cylindrical guide is fitted over the forward projection of the catheter body, and in this state, an outer polymer layer is coated on the outer surface of the catheter body. Thereafter, the guide is removed whereby the forward projection of the outer polymer layer can be spaced apart from the forward projection of the catheter body.

Figure 19A:
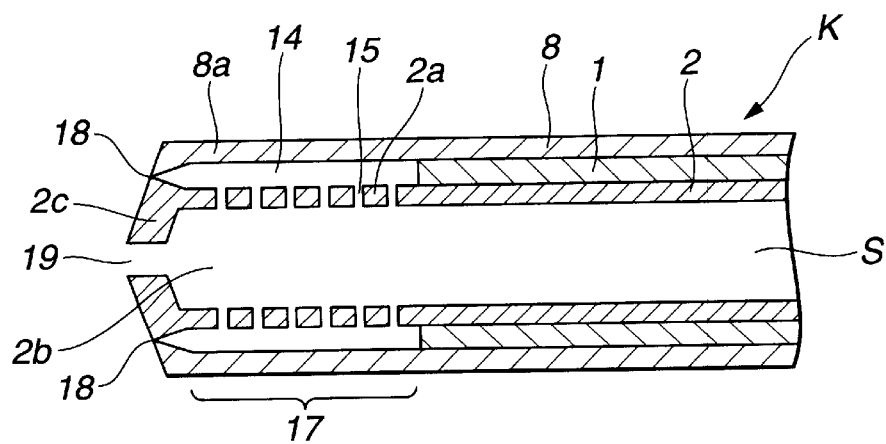
FIGS. 19(A) to (C) illustrate a catheter according to a third example of the invention, FIG. 19(B) being a fragmentary cross-sectional view showing the catheter whose distal opening is closed with a guide wire, FIG. 19(C) being a fragmentary cross-sectional view showing the catheter whose distal end portion is dilated.
Figure 19B:
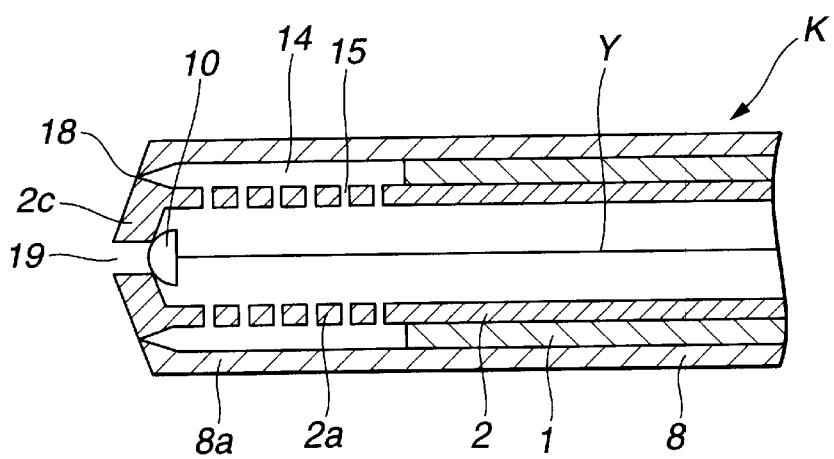
Figure 19C:
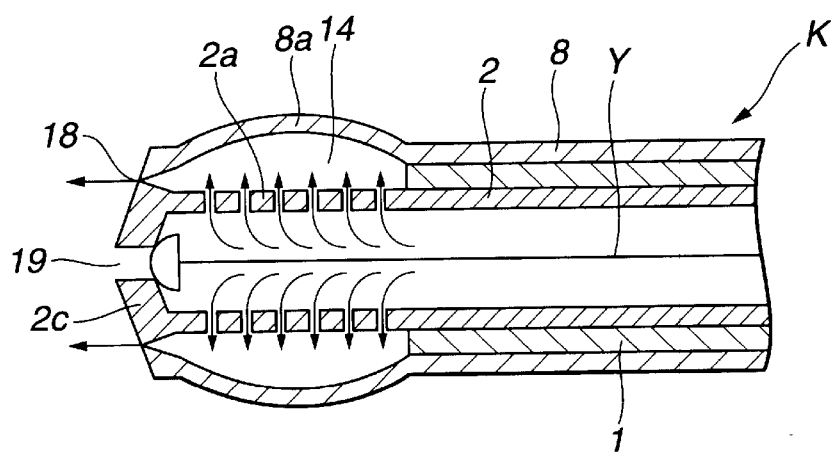

FIGS. 19(A) to 19(C) illustrate a catheter K having a space defined in its distal end portion according to a third example. In this catheter K, the forward projection 2*a* of the inner polymer layer 2 is provided along the distal end inner periphery with a approximately annular cover 2*c* having a distal opening 19, through which the catheter lumen (the hollow portion 2*b* of the inner polymer layer) is in communication with the outside of the catheter distal end. The distal opening of the space 14 constitutes an annular discharge part 18. The remaining constructions are the same as in the first example. It is noted that the discharge part 18 may be used as discharge lumen as in the first example or closed.

On use of the catheter of the third example, as shown in FIG. 19(B), a guide wire Y having a approximately hemispherical head 10 at a distal end for closing the distal opening 19 of the hollow portion 2*b* of the inner polymer layer is inserted into the catheter whereby the distal opening 19 is closed with the head 10. In this state, an injection fluid such as saline, an embolic material or a contrast medium is injected into the catheter lumen S for dilating outward the distal end portion (specifically the forward projection 8*a* of the outer polymer layer). With the dilated state kept, the injection fluid such as an embolic material is discharged through the discharge part (or discharge lumen) 18 as shown in FIG. 19(C). In some cases, the distal opening 19 may be closed.

At least a distal end portion of the guide wire Y used in combination with the catheter of the third example is preferably formed of a shape memory-specialized alloy having shape memory property, but free from superelasticity or pseudoelasticity at least at the body temperature (typically about 33 to 42° C., preferably in the range of 35 to 38° C.).

The preferred metal is such that when at least the distal end portion of the guide wire body is deformed at the body temperature, restoration takes not less than 0.3 second, preferably not less than 0.5 second, more preferably not less than 1 second and further preferably not less than 2 seconds.

Figure 20:
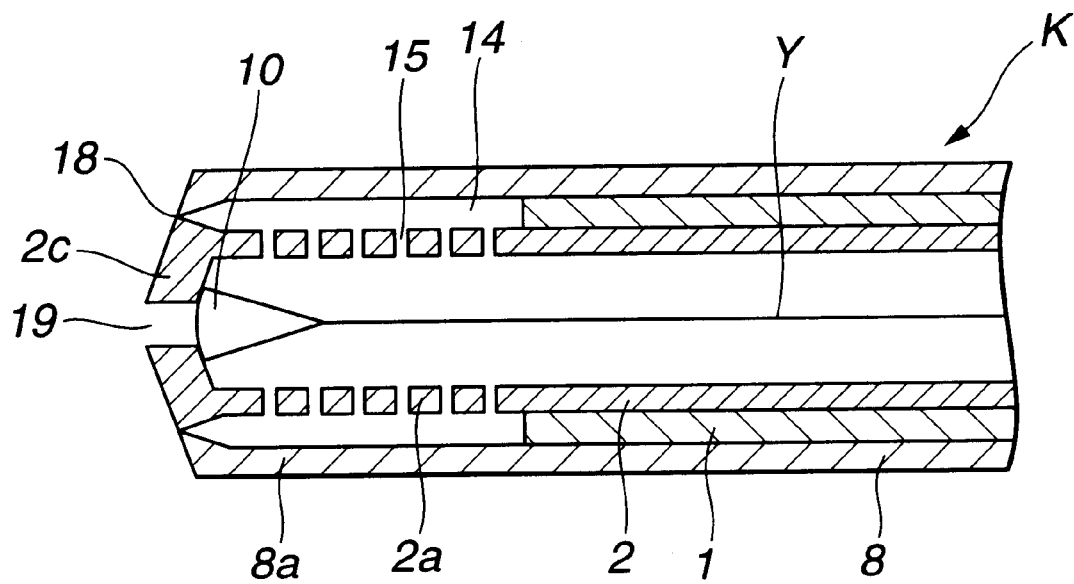
FIG. 20 is a fragmentary cross-sectional view showing the catheter whose distal opening is closed with a different guide wire.
Figure 21:
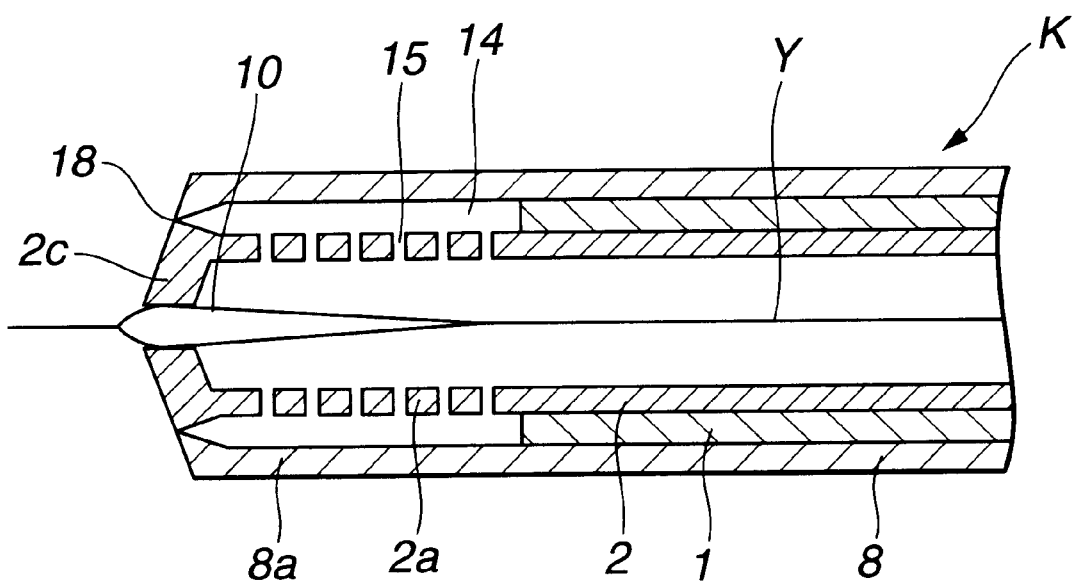
FIG. 21 is a fragmentary cross-sectional view showing the catheter whose distal opening is closed with another different guide wire.

The distal head 10 of the guide wire Y is not critical in shape insofar as the distal opening 19 of the catheter can be closed therewith. The head may be configured to a approximately hemispherical shape as shown in FIGS. 19(B) and 19(C), a approximately conical shape as shown in FIG. 20, or a shape gradually dilating to a sufficient diameter to close the opening as shown in FIG. 21. Herein, the distal head 10 of the guide wire may be formed of the above-described shape memory-specialized alloy although it is preferable from the molding and economic standpoints to form the head from a resin.

In the catheters of the second and third examples, the extent of dilation of the distal end portion and other constructions may be the same as in the first example.

Also in the catheter of this embodiment, like the second embodiment, a metal layer may be formed on the inner and/or outer surface of the catheter body. In the event that the injection fluid such as saline, an embolic material and a contrast medium discharged from the catheter distal end adheres to the catheter distal end so that the catheter cannot be withdrawn, then the catheter distal end portion (specifically the forward projections of the inner and outer polymer layers) can be cut off by conducting high frequency current through the metal layer formed on the inner and/or outer surface of the catheter body or the guide wire. The catheter has thus highly improved safety.

Unlike the conventional balloon catheter having an inflating balloon at a distal end, the catheter of the present invention is constructed such that the distal end portion of the catheter itself is provided with an inflating space or gap, the space or gap is filled with an injection fluid such as saline, an embolic material and a contrast medium whereby the catheter distal end portion is outwardly dilated. This eliminates a need for an extra balloon and an extra introduction path for inflating the balloon, allows the catheter to be formed to a small diameter, and ensures that blood or fluid flow is blocked in a safe and reliable manner. The provision of discharge lumen in communication with the space or gap opening at the catheter distal end (or lid) enables that an embolic material or contrast medium be discharged to the lesion while maintaining the distal end portion dilated and the blood or fluid flow blocked, and thus enables angiography and embolization at the lesion in a safe and reliable manner.

There has been the third embodiment of the invention although the invention is not limited to the illustrated examples, and various changes may be made thereto insofar as the objects of the invention are achievable.

Fourth Embodiment of the Invention

The fourth embodiment of the invention provides a catheter comprising a catheter body and an outer polymer layer covering the outer surface of the catheter body, characterized in that the catheter body is provided with at least one slit extending axially from the distal end of the catheter body, and the gap of the slit is narrowed such that the catheter body is reduced in diameter toward the distal end. This catheter eliminates an introducing tube by thermoplastic resin, is improved in operation and safety, and is improved in manufacture cost performance in that the catheter diameter can be readily adjusted in accordance with the size of the destination.

The catheter body used herein may be formed using any of tubes of flexible thermoplastic resins such as polystyrene, polyolefin, polyester, and polyurethane, and metallic tubes of stainless steel and shape memory alloys and the like, which are conventionally used to form catheter bodies. For achieving the objects and benefits of the invention to the maximum extent, it is preferred that at least a distal end portion of the catheter body be formed of a shape memory-specialized alloy having shape memory property, but free from superelasticity or pseudoelasticity at least at the body temperature (typically about 33 to 42° C., and preferably in the range of 35 to 38° C.), as in the first embodiment.

It is preferred herein that when at least the distal end portion of the catheter body is deformed at the body temperature, restoration takes not less than 0.3 second. Also, at least the distal end portion of the catheter body is preferably formed of a metal material which exhibits a yield force of not higher than 8.8 N, a recovery force of not higher than 2.9 N, and a residual strain of not less than 0.2 mm when a three-point bending test is carried out on a metal tube having an outer diameter of 875 $\mu$m and an inner diameter of 750 $\mu$m. Notably, the preferred range of the results of the catheter body in the three-point bending test is the same as in the first embodiment.

Figure 22:
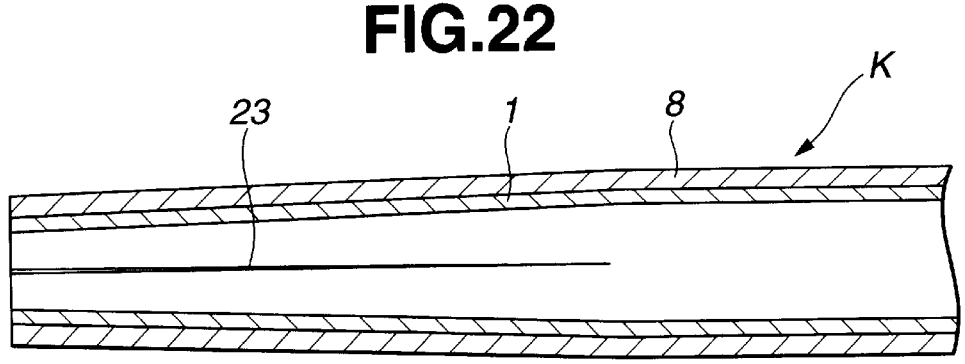
FIG. 22 is a cross-sectional view of a catheter body according to a further embodiment of the invention.

In the catheter K of this embodiment, as shown in FIG. 22, an outer polymer layer 8 is formed by coating on the outer surface of a catheter body 1, and the catheter body 1 is provided with at least one slit 23 extending axially from the distal end of the catheter body 1. Herein, the wall thickness of the catheter body 1 is preferably about 20 to 200 $\mu$m and uniform from the distal end toward the proximal end of the catheter body. This range of thickness is effective for preventing the probable breakage of the catheter body due to the provision of slits.

Figure 23A:
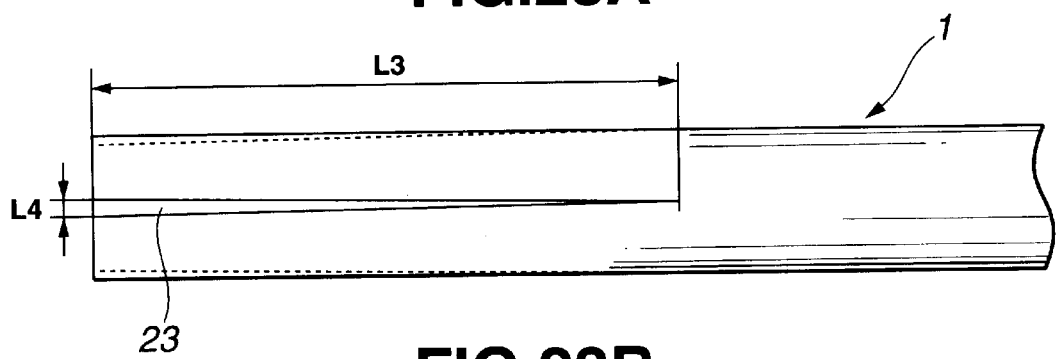
FIGS. 23(A) and 23(B) are side and front views of the same catheter body.
Figure 23B:
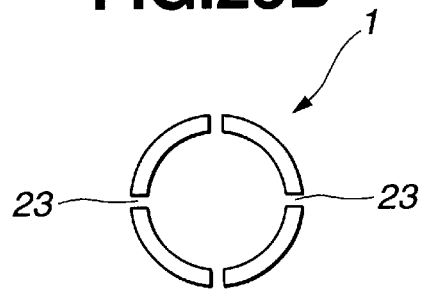

At least one, preferably at least two, and more preferably two to eight slits 23 are formed in the catheter body 1 so as to extend axially from the distal end as shown in FIG. 23(A). Where two or more slits 23 are formed, they are preferably located at diametrically symmetric positions as shown in FIG. 23(B). In the example shown in FIG. 23, four slits 23 are formed in the catheter body 1.

Figure 24:
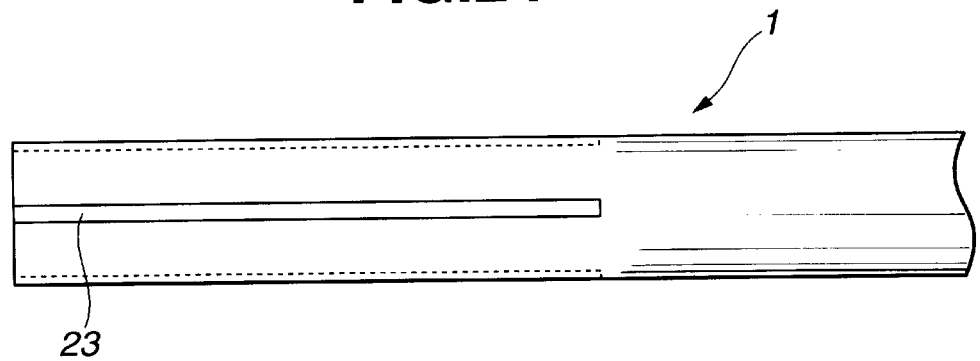
FIG. 24 is a side view of another catheter body.

The slit 23 is preferably of approximately rectangular or wedge shape in a side view as shown in FIGS. 23 and 24. Specifically, the slit 23 is preferably formed such that the distance of the slit gap is gradually reduced from the distal end toward the proximal end of the catheter body. By narrowing the slit gap, there is obtained a catheter whose diameter gradually reduces from the proximal end toward the distal end. In some cases, while the gap of the slit in the catheter body is kept constant without narrowing, a polymer layer is coated on the catheter body whereby the catheter is endowed with flexibility.

As shown in FIG. 23, the slits 23 (slit body portion) have an axial length L3 of not shorter than 2 cm, preferably not shorter than 5 cm, more preferably not shorter than 10 cm, further preferably not shorter than 20 cm, and most preferably not shorter than 40 cm from the distal end of the catheter body, and preferably not longer than 100 cm at the maximum.

The width L4 of the slits 23 is generally about 1 to 2000 $\mu$m, preferably 10 to 1,500 $\mu$m at the catheter distal end, although the width is indefinite because it varies with the shape and number of slits, the inner diameter of the catheter, and the inner diameter of the catheter after adjustment.

In the catheter of this embodiment, slits are preferably formed in a distal portion of the catheter body and an intermediate portion following the distal portion such that more slits are formed in the distal portion than in the intermediate portion. In the catheter shown in FIG. 25, for example, the number of slits formed in the distal portion is greater than the number of slits formed in the intermediate portion by at least one, preferably at least two. Additionally, the gap of slits formed in the distal and intermediate portions is narrowed toward the distal end so that the catheter body is reduced in diameter in two stages.

Figure 25:
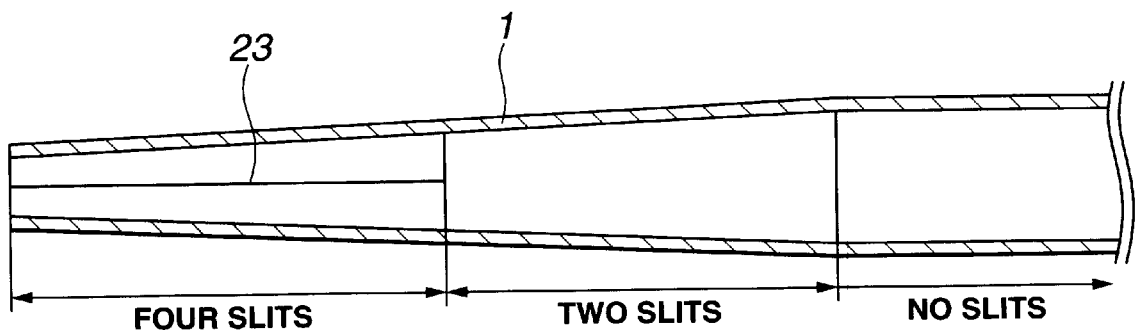
FIG. 25 is a cross-sectional view of a catheter body whose inner diameter is adjusted in two stages.

It is noted that in FIG. 25, a portion of the catheter body extending less than 15 cm from the distal end (i.e., distal portion) is formed with four slits 23, and a portion of the catheter body spaced not less than 15 cm from the distal end (i.e., intermediate portion) is formed with two slits 23 (not seen). Herein, the distal portion of the catheter body designates a portion of the catheter body that extends less than 15 cm from the distal end, and the intermediate portion designates a portion of the catheter body that is spaced not less than 15 cm from the distal end. The distal portion of the catheter body is formed with at least two slits, preferably at least four slits, and more preferably four to eight slits, and the intermediate portion is formed with at least one slit, preferably at least two slits, and more preferably two to four slits.

The catheter wherein more slits are formed in the distal portion than in the intermediate portion of the catheter body and the gaps of the slits in the distal and intermediate portions are narrowed so that the diameter is reduced toward the distal end in two stages has the advantage that the distal end portion of the catheter can be adjusted to a smaller diameter, and the catheter can have a diameter corresponding to the inner diameter of a fine blood vessel or ureter. Similarly, a catheter whose diameter changes in three stages can be fabricated by dividing the catheter body into three stages from the distal end, a first stage extending less than 10 cm from the distal end, a second stage extending from 10 cm to less than 20 cm, and a third stage extending from 20 cm to less than 30 cm, and reducing the number of slits as the stage approaches the distal end.

The method of forming the slits is not critical. In case wherein the catheter body is made of a metal, for example, the slits can be formed by etching, electric discharge machining, electron beam working, laser working, machining (such as cutting) and a combination thereof. In case wherein the catheter body is made of a resin, the slits can be formed by integral molding in a mold, machining (such as cutting) and a combination thereof.

Figure 26:
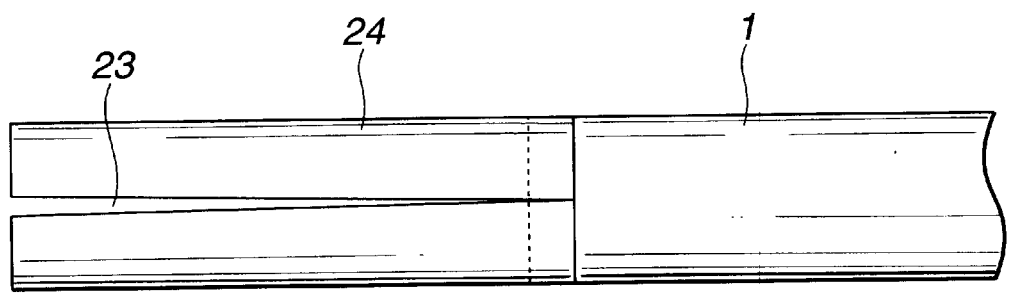
FIG. 26 is a side view showing a method of forming slits.
Figure 27:
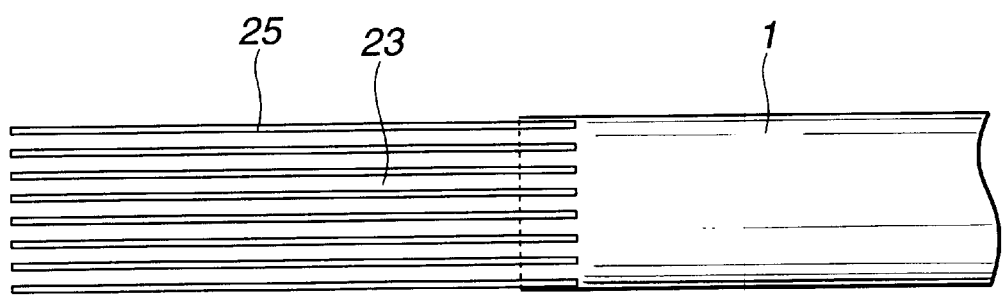
FIG. 27 is a side view showing another method of forming slits.

In some cases, as shown in FIG. 26, a nose piece 24 in which slits can be formed is prepared in advance, the fragmental part 24 is joined to the distal end of a catheter body 1 as by welding or adhesive bonding, and the slits 23 are formed. Alternatively, as shown in FIG. 27, wire-like parts 25 may be placed around and extended from the distal end of a catheter body 1 to define the slits 23.

Figure 28A:
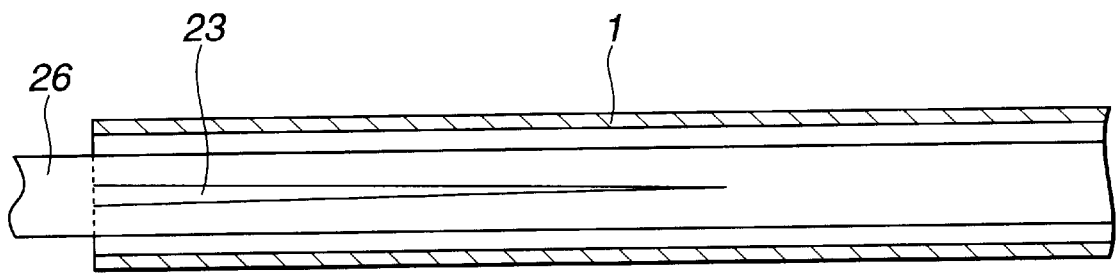
FIG. 28(A) being a cross-sectional view showing the slit catheter body with a guide tube inserted therein.
Figure 28B:
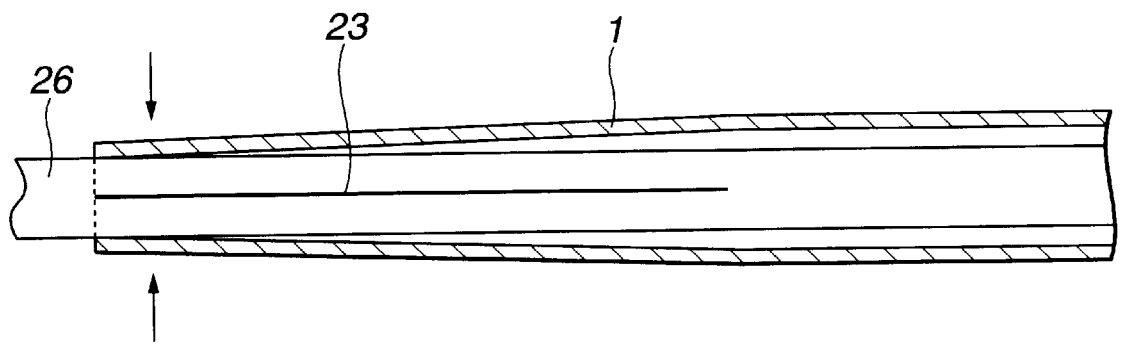
FIG. 28(B) being a cross-sectional view in which the gap of slits is narrowed in conformity with the guide tube.
Figure 28C:
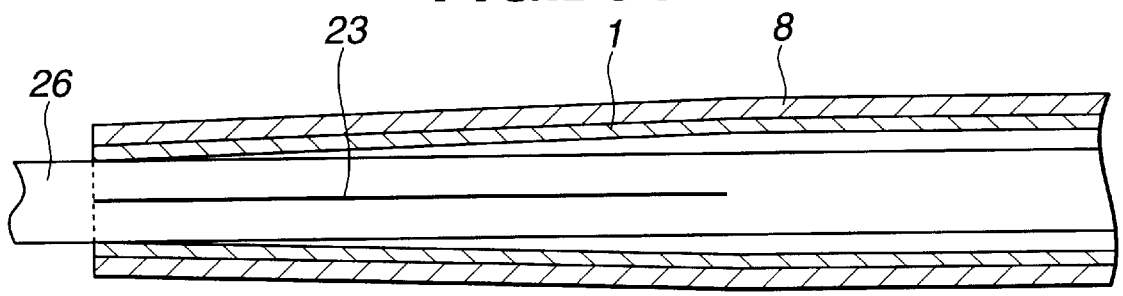
FIG. 28(C) being a cross-sectional view showing the catheter body which is coated on its outer surface with an outer polymer layer.

Next, the catheter having slits according to this embodiment is fabricated as shown in FIGS. 28(A) to 28(C). A guide tube or guide rod 26 having an outer diameter equal to the inner diameter of the catheter is inserted into the lumen of a catheter body 1 having slits 23 formed therein as shown in FIG. 28(A). The gaps of the slits 23 in the catheter body 1 are narrowed in the direction of an arrow in conformity with the guide tube or guide rod 26 as shown in FIG. 28(B) whereby the catheter body 1 is configured so as to gradually decrease in diameter toward the distal end. Thereafter, as shown in FIG. 28(C), an outer polymer layer 8 is coated on the outer surface of the catheter body 1. In this way, the catheter whose distal end portion (extending, at least not shorter than 2 cm from the distal end) has a desired inner diameter can be fabricated.

Though not shown, on the inner surface of the catheter body, especially the inner surface of the slit region, an inner polymer layer is preferably formed by coating a thermoplastic resin such as polyurethane, nylon or polyolefin or inserting an inner polymer tube. Where the slit region is short, it suffices that the inner surface of the catheter body is merely polished.

Figure 29:
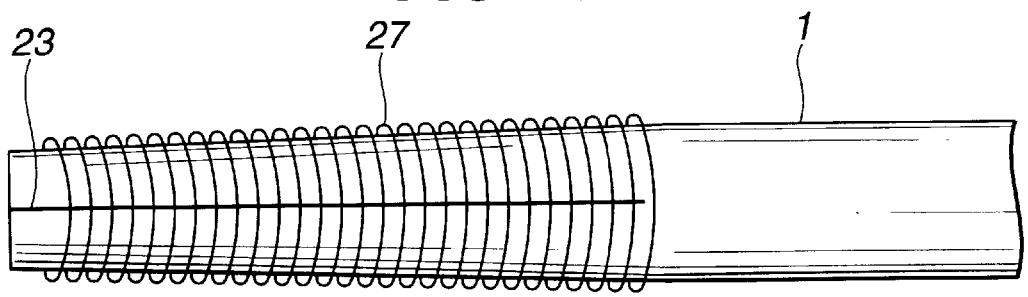
FIG. 29 is a side view in which a slit portion is reinforced by coil winding.

In the practice of the invention, the distal end portion of the catheter body is provided with slits and a linear elastic material selected from among a metal wire, organic wire and inorganic wire is wound in a coil fashion and/or braided in a mesh fashion around the slit region, or attaching a linear material along the axial direction, or any combination of the above. This is preferable because the distal end portion of the catheter body is reinforced and endowed with sufficient flexibility to prevent breakage. For example, as shown in FIG. 29, slits are formed in a region of the catheter body 1 so that the catheter body is reduced in diameter toward the distal end, and a linear elastic material 27 selected from among a metal wire, organic wire and inorganic wire is externally wound around the slit region in a coil fashion to reinforce the distal end portion and impart flexibility thereto.

The linear elastic material selected from among a metal wire, organic wire and inorganic wire may be the same as in the second embodiment.

Simply after manufacturing catheter bodies having one or two basic inner diameters (e.g., an inner diameter of 400 $\mu$m, 500 $\mu$m or 600 $\mu$m), they can be freely tailored into catheter bodies of plural types each having a diameter corresponding to the inner diameter of the destination, by providing the slits as mentioned above. For example, when it is desired to fabricate catheter bodies of three types having an inner diameter of 300 $\mu$m, 400 $\mu$m, and 500 $\mu$m, only by manufacturing catheter bodies having an inner diameter of 500 $\mu$m, they can then be tailored into catheter bodies whose distal end portion has an inner diameter of 300 $\mu$m or 400 $\mu$m, by forming slits in the catheter bodies and narrowing the gap of the slits. Also in the case of a hub to be attached to a proximal end portion of the catheter, it is sufficient to manufacture only hubs having one or two basic inner diameters, and then there is no need to furnish hubs of plural diameters corresponding to catheter diameters. The catheter of the present invention is drastically improved in manufacture cost performance over the prior art catheters.

The invention enables to fabricate even catheter bodies whose distal end portion (extending at least 2 cm from the distal end) has an ultrathin diameter which are very difficult to fabricate in the prior art, for example, catheter bodies having an inner diameter of 200 $\mu$m and an outer diameter of 300 $\mu$m and catheter bodies having an inner diameter of 100 $\mu$m and an outer diameter of 200 $\mu$m.

The structure of the catheter is the same as in the first and second embodiments. The description of those parts represented by like numerals is omitted. The thickness of the catheter body 1, outer polymer layer 8 and inner polymer layer 2 and the inner diameter of the catheter are the same as in the first embodiment.

There has been the fourth embodiment of the invention although the invention is not limited to the illustrated examples, and various changes may be made thereto insofar as the objects of the invention are achievable.

Fifth Embodiment of the Invention

The fifth embodiment of the invention provides a guide wire comprising a guide wire body and a distal head and adapted to be inserted into a catheter lumen, characterized in that the distal head of the guide wire is configured to a shape capable of pushing an embolic material such as a coil, and at least a distal portion of the guide wire body is formed of a shape memory-specialized alloy having shape memory property, but free from superelasticity or pseudoelasticity at least at the body temperature. This guide wire ensures safe and reliable embolization and angiography.

Figure 30:
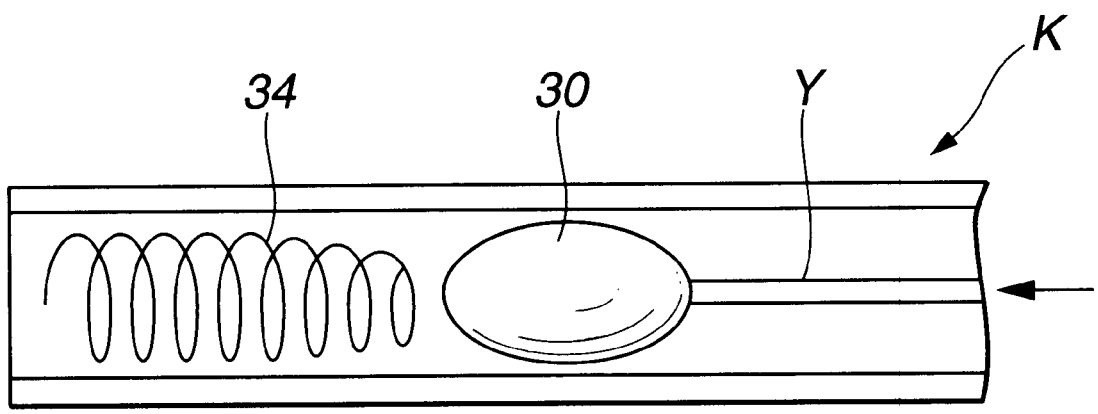
FIG. 30 schematically illustrates how to push out an embolic material such as a coil using a guide wire according to the invention.
Figure 31:
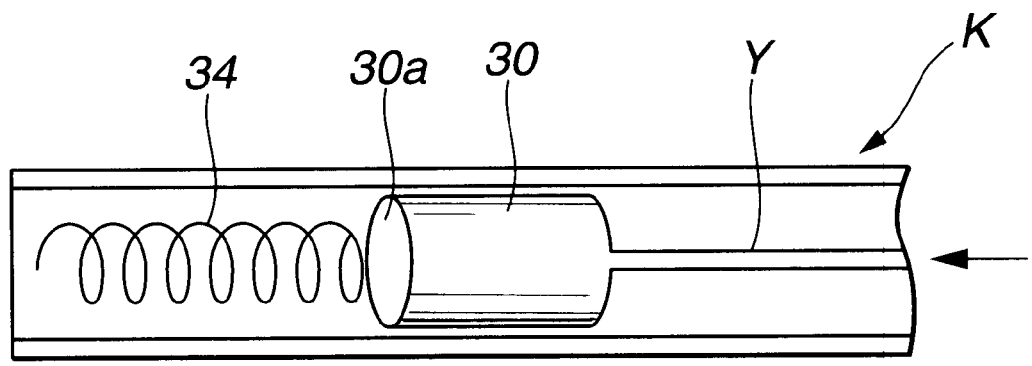
FIG. 31 schematically illustrates another guide wire according to the invention.

The guide wire or coil pusher of this embodiment is mainly advantageously used in the embolization of artery/vein teratosis and aneurysm in the brain, heart and abdomen and so on. As shown in FIGS. 30 and 31, the guide wire Y has at a distal end a head 30 capable of pushing out an embolic material 34 such as a coil. The distal head 30 of the guide wire Y may be formed of the above-described shape memory-specialized alloy although it is preferable from the molding and economic standpoints to form the head from a resin. The shape of the distal head 30 is not critical and may be generally spherical as shown in FIG. 30. Alternatively, the head 30 has a distal end face 30a which is configured concave in conformity with the embolic material such as a coil to ensure that the embolic material such as a coil is pushed out as shown in FIG. 31.

The shape memory-specialized alloy of which the guide wire body is constructed is preferably such that when at least a distal end portion (at least a portion extending 5 mm from the distal end, and especially a portion extending 30 cm from the distal end) of the guide wire body is deformed at least at the body temperature (typically about 33 to 42° C., and preferably in the range of 35 to 38° C.), the restoration takes a time of not shorter than 0.3 second, preferably not shorter than 0.5 second, more preferably not shorter than 1 second, further preferably not shorter than 1.5 seconds.

More particularly, the results of the three-point bending test on a guide wire body differ with the outer diameter of the guide wire body, with the preferred range being shown below.

<Guide Wire Body with an Outer Diameter of 600 to 800 $\mu$m>

(i) The yield force is not higher than 9.8 N, preferably not higher than 6.4 N, more preferably not higher than 5.4 N, further preferably not higher than 4.4 N, and most preferably not higher than 2.9 N.

(ii) The recovery force is not higher than 3.9 N, preferably not higher than 2.9 N, more preferably not higher than 1 N, and further preferably not higher than 0.5 N.

(iii) The residual strain is not less than 0.2 mm, preferably not less than 0.5 mm, more preferably not less than 0.9 mm, and further preferably not less than 1.2 mm.

<Guide Wire Body with an Outer Diameter of 300 $\mu$m to Less than 600 $\mu$m>

(i) The yield force is not higher than 7.8 N, preferably not higher than 4.9 N, more preferably not higher than 3.9 N, further preferably not higher than 2.9 N, and most preferably not higher than 2 N.

(ii) The recovery force is not higher than 2.9 N, preferably not higher than 1 N, more preferably not higher than 0.5 N, and further preferably not higher than 0.1 N.

(iii) The residual strain is not less than 0.2 mm, preferably not less than 0.5 mm, more preferably not less than 0.9 mm, and further preferably not less than 1.2 mm.

<Guide Wire Body with an Outer Diameter of Less than 300 $\mu$m>

The yield force is preferably not higher than 2 N, more preferably not higher than 0 to 1 N; the recovery force is preferably not higher than 2 N, more preferably not higher than 0 to 1 N; and the residual strain is preferably not less than 0.1 mm, more preferably not less than 0.9 mm.

Since at least a distal end portion (at least a portion extending 5 mm from the distal end, and especially a portion extending 30 cm from the distal end) of the guide wire body is formed of a shape memory-specialized alloy having shape memory property, but free from superelasticity or pseudoelasticity at least at the body temperature, the guide wire of this embodiment can be smoothly inserted even into a complex tortuous thin wall vessel, ureter, pancreatic duct or bile duct and so on without snagging of the guide wire with the catheter lumen or breaking, ensuring that the bulged distal head pushes out the embolic material such as a coil to implant it at the destination.

The catheter through which the guide wire of this embodiment can be inserted on use is not critical although use is preferably made of the catheter of any of the foregoing first to fourth embodiments which can be smoothly introduced even into a complex tortuous thin wall vessel, ureter, pancreatic duct or bile duct.

Next, the foreign matter retrieving/recovering or calculus capturing catheter of the invention has an operating part (or guide wire body) inserted through its lumen, the operating part having means disposed at the distal head for capturing a calculus or retrieving and recovering a foreign matter.

Also in this embodiment, at least a distal end portion of each of the catheter body and guide wire body is preferably formed of a shape memory-specialized alloy having shape memory property, but free from superelasticity or pseudoelasticity at least at the body temperature (typically about 33 to 42° C., and preferably in the range of 35 to 38° C.). It is preferred herein that when at least the distal end portion of each of the catheter body and guide wire body is deformed at the body temperature, restoration takes not shorter than 0.3 second. Also, the preferred range of the results of a three-point bending test on each of the catheter body and guide wire body is as described above. When the operating part (guide wire body) consists of two or more pieces of wires, the bundle of these must satisfy the above requirements.

The foreign matter retrieving/recovering means or calculus capturing means attached to the distal end of the guide wire is not critical. For example, preferred is a capture means in the form of a shape memory alloy such as Ni—Ti alloy which undergoes plastic deformation below the transformation temperature and restores the shape capable of surrounding and capturing a calculus or foreign matter when heated above the transformation temperature.

Figure 32A:
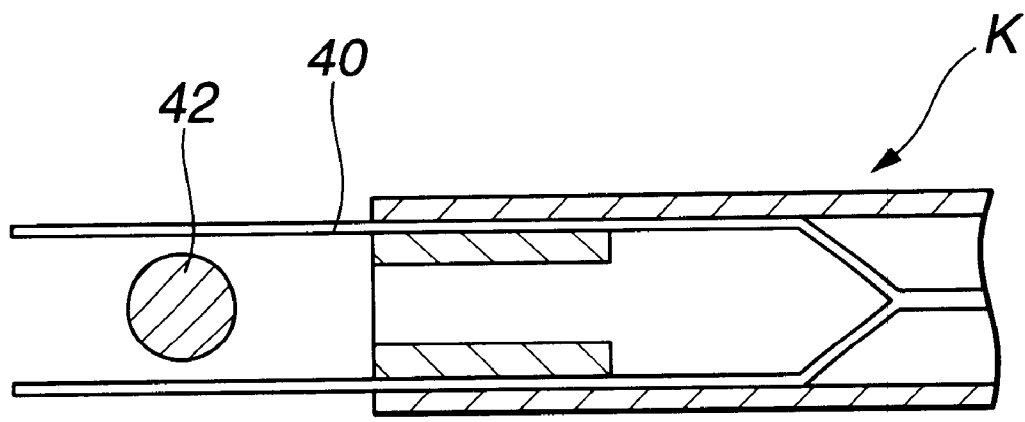
FIGS. 32(A) and (B) schematically illustrate one way of capturing a calculus or foreign matter using a foreign matter retrieving/recovering or calculus capturing catheter according to the invention.
Figure 32B:
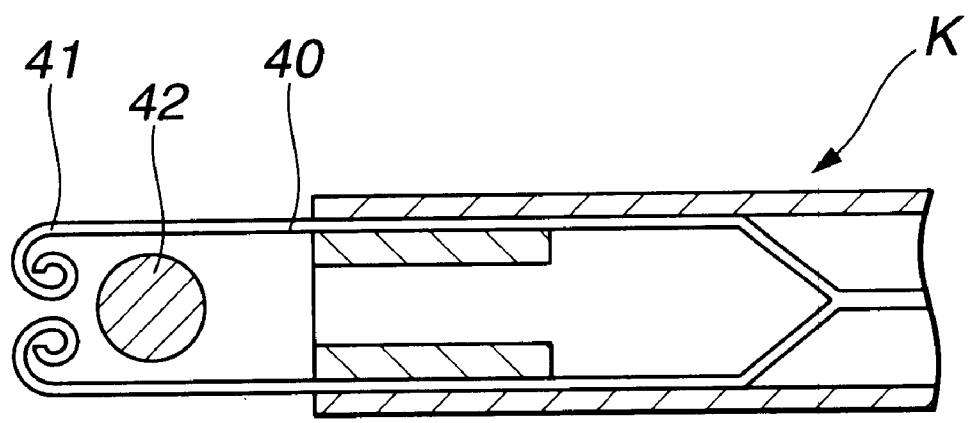

More particularly, as shown in FIGS. 32(A) and 32(B), the capture means 41 made of a shape memory alloy consists of four operating wires 40 (only two are shown in the figure) whose distal end portions are shape memorized so as to become coiled upon heating. On use of the catheter K in which the operating part having the capture means 41 at the distal end is inserted, when the distal end reaches the position of calculus or foreign matter, the operating wires 40 are forced out until the capture means 41 is extended beyond the calculus or foreign matter 42. In this state, by conducting electricity through or heating the operating wires 40, the capture means 41 is deformed into a coiled shape to capture the calculus or foreign matter 42. It is noted that the shape of the capture means after restoration is not critical insofar as the calculus or foreign matter can be captured. Any of various shapes including key and helical shapes may be used. The number of operating wires is at least two, and preferably two to ten.

Figure 33A:
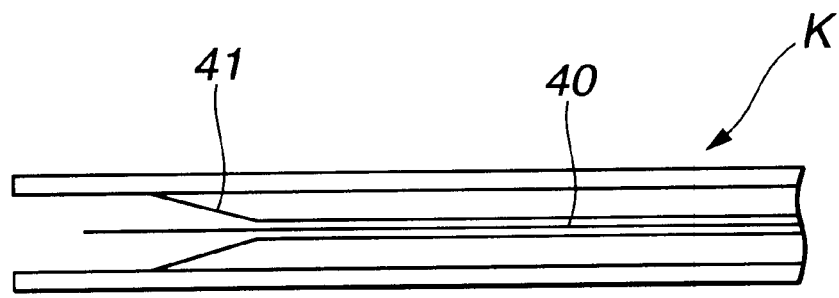
FIGS. 33(A) to (C) schematically illustrates another way of capturing a calculus or foreign matter.
Figure 33B:
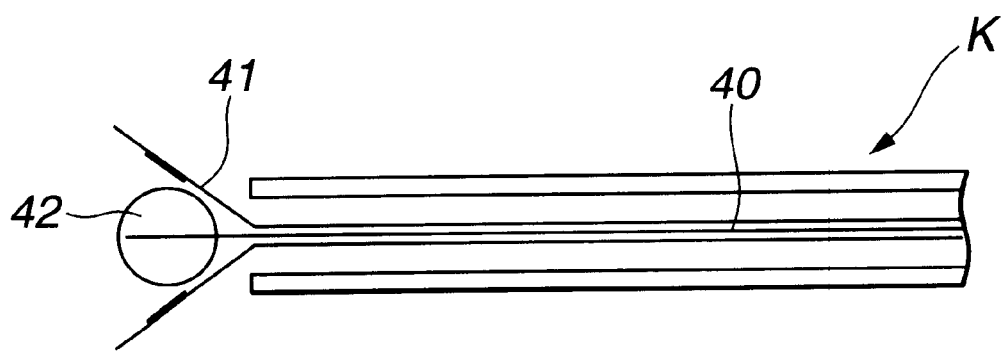
Figure 33C:
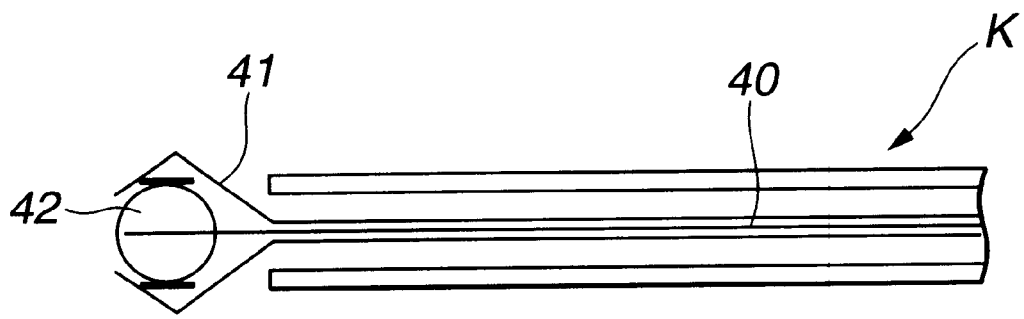

FIGS. 33(A) to 33(C) illustrate another capture means. The capture means 41 made of a shape memory alloy is received within the catheter K in contracted state until the position of calculus or foreign matter is reached. When the distal end of the catheter reaches the position of calculus or foreign matter, the operating wire 40 is forced out whereby the capture means 41 is spontaneously spread due to the action of plate springs to take a shape capable of enclosing the calculus or foreign matter 42. In this state, by conducting electricity through or heating the operating wire 40, the capture means 41 is constricted to capture the calculus or foreign matter 42.

Figure 34A:
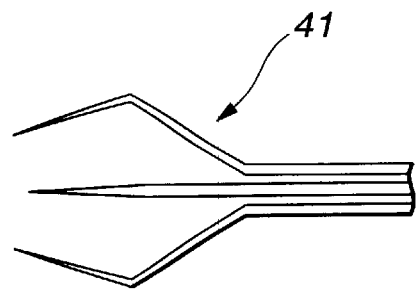
FIGS. 34(A) to (E) schematically illustrates a further way of capturing a calculus or foreign matter.
Figure 34B:
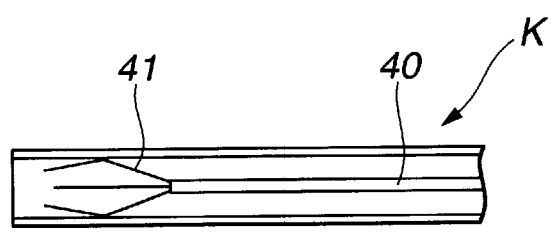
Figure 34C:
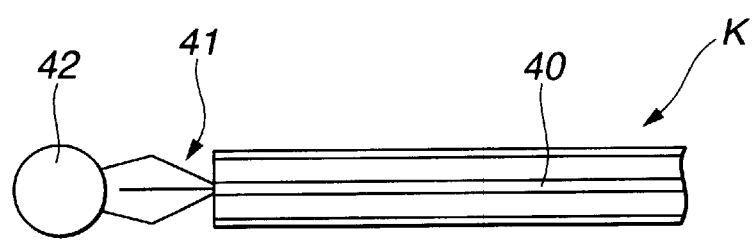
Figure 34D:
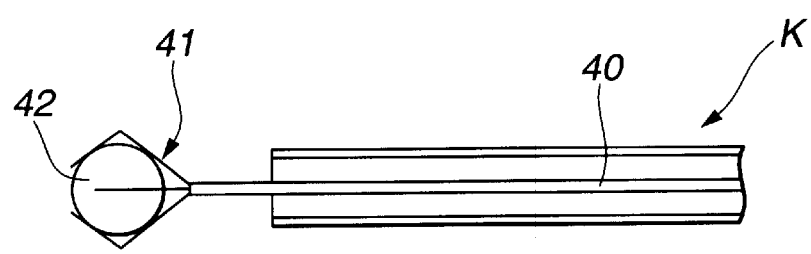
Figure 34E:
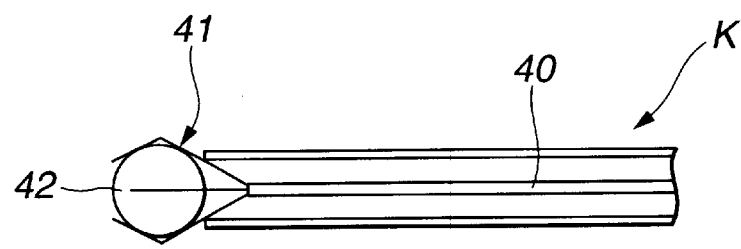

FIG. 34(A) illustrates the capture means 41 consisting of four wires which are previously shape memorized to a constricted shape capable of enclosing a calculus or foreign matter. As shown in FIGS. 34(B) to 34(E), this capture means 41 is received within the catheter K until the position of calculus or foreign matter is reached. When the distal end of the catheter reaches the position of calculus or foreign matter, the operating wire 40 is forced out whereby the capture means 41 is spontaneously spread to enclose and grip the calculus or foreign matter 42 for capturing it.

Figure 35:
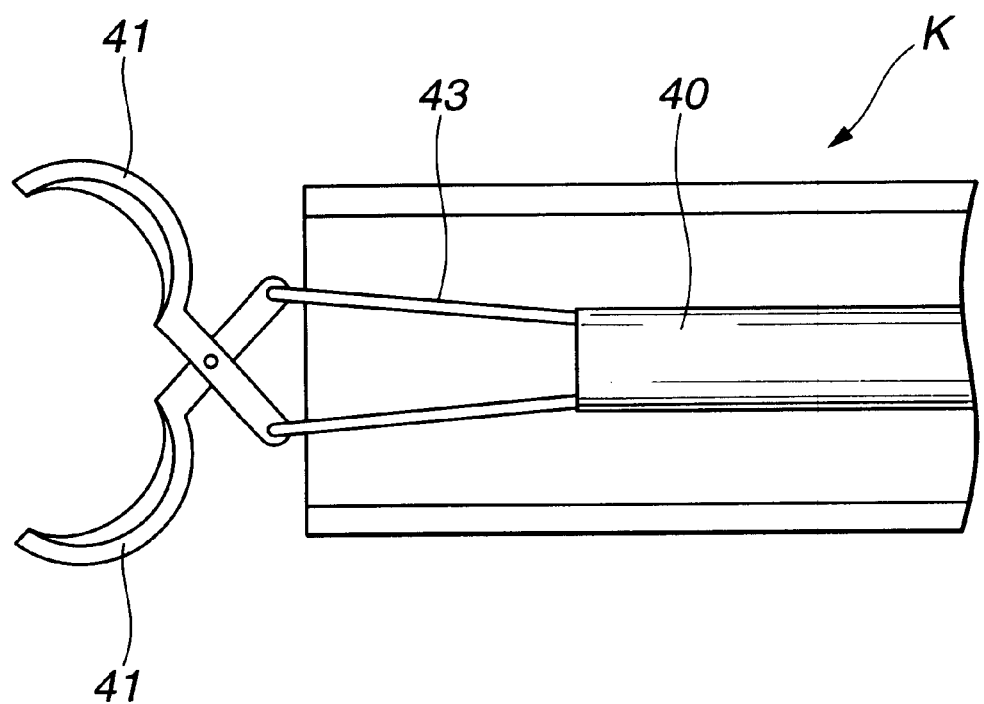
FIG. 35 conceptually illustrates means for capturing a calculus or foreign matter according to the invention.

FIG. 35 illustrates the capture means 41 consisting of a pair of arcuate arms which can be opened and closed. This capture means is constructed such that when the position of calculus or foreign matter is reached, two shafts 43, 43 extending from an operating part 40 are pulled, whereby the arcuate arms 41 are closed to capture the calculus or foreign matter. The shape of the arcuate arms is not critical. They may be configured as a pair of cups.

Figure 36:
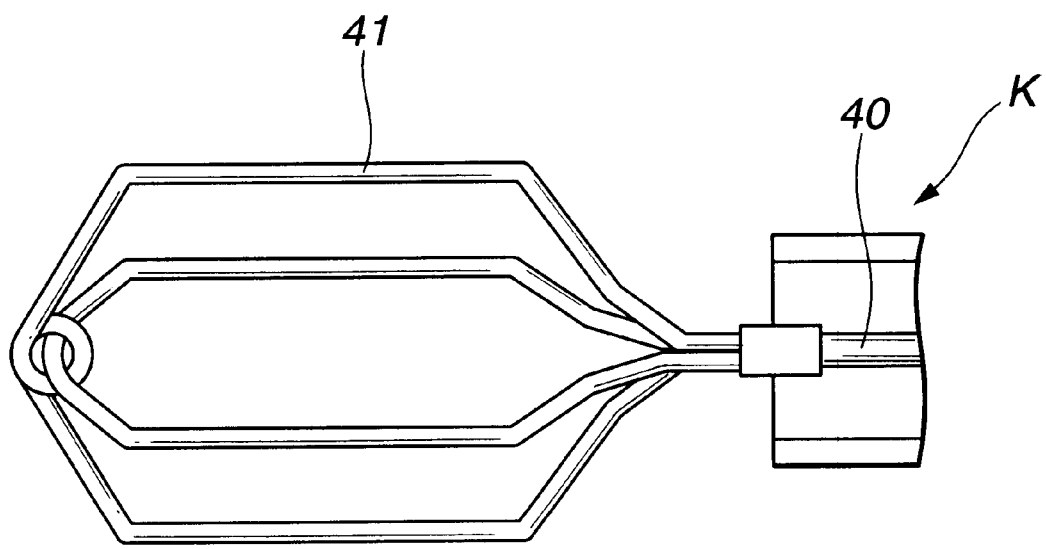
FIG. 36 conceptually illustrates another means for capturing a calculus or foreign matter.
Figure 37:
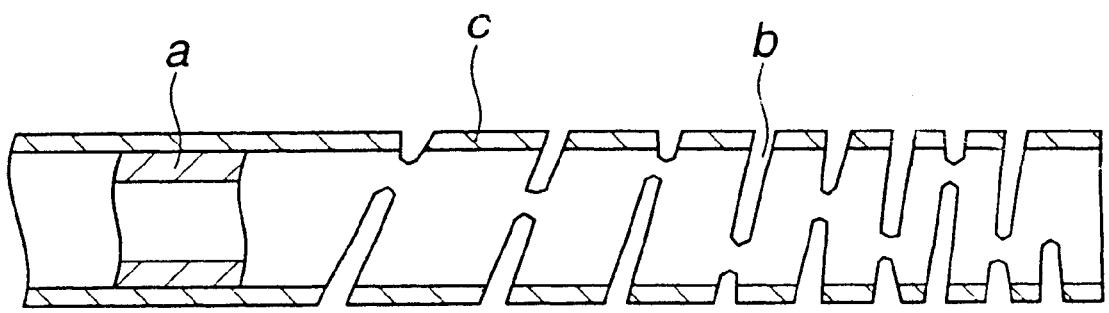
FIG. 37 is a cross-sectional view of a prior art catheter whose distal end portion is formed with grooves.
Figure 38:
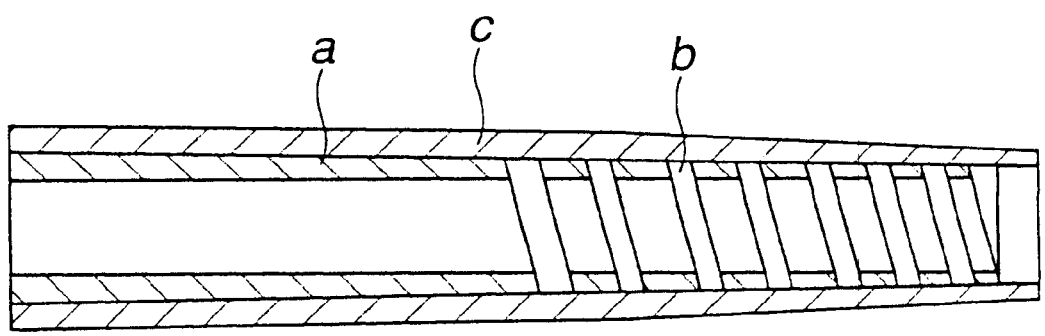
FIG. 38 is a cross-sectional view of another prior art catheter.

FIG. 36 illustrates the capture means 41 which is configured to a basket-like barrel shape using four elastic wires. At the destination, the operating wire 40 is forced out to expand the capture means 41 into a basket shape within which calculus or foreign matter is caught. The number of elastic wires is four to ten.

In the foreign matter retrieving/recovering or calculus capturing catheter of the invention, at least the distal end portion of each of the catheter body and operating part (guide wire body) having the foreign matter retrieving/recovering or calculus capturing means is formed of a shape memory-specialized alloy having shape memory property, but free from superelasticity or pseudoelasticity at least at the body temperature. As a result, the catheter of the present invention can smoothly convey the foreign matter retrieving/recovering or calculus capturing means to the position of calculus or foreign matter even through a complex tortuous fine ureter without causing damage to the ureter, although prior art catheters encounter difficulty in such operation. This can take full advantage of the foreign matter retrieving/recovering or calculus capturing means, with excellent results of foreign matter removal/recovery or calculus capture being obtained.

There has been the fifth embodiment of the invention although the invention is not limited to the illustrated examples, and various changes may be made thereto insofar as the objects of the invention are achievable.

EXAMPLES

Examples of the invention and Comparative Examples are given below by way of illustration, and not by way of limitation.

Example 1 and Comparative Example 1

A tubular member of a Ni—Ti alloy with a nickel content of 49 to 58 atomic % was cold worked and drawn in a conventional manner, forming a catheter body having an outer diameter of 875 µm, an inner diameter of 750 µm, and a thickness of about 63 µm. The catheter body was heat-treated at 400° C. for 10 to 30 minutes.

A distal end portion of the catheter body which extended 30 cm from the distal end was heat-treated in argon gas at 450° C. for 1 to 10 hours, and a distal end portion of the catheter body which extended 12.5 cm from the distal end was heat-treated in argon gas at 400° C. for 24 hours. This resulted in a catheter body formed of a shape memory-specialized alloy having shape memory property, but free from superelasticity or pseudoelasticity at the body temperature in which the proximal end side of the catheter body has relatively high rigidity and suppleness while the distal end side of the catheter body has flexibility as the region approaches the distal end (Example 1).

For comparison purposes, a tubular body of a Ni—Ti alloy with a nickel content of 49 to 58 atomic % was cold worked and drawn in a conventional manner, forming a catheter body having an outer diameter of 875 µm, an inner diameter of 750 µm, and a thickness of about 63 µm. Simply by heat-treating the catheter body at 400° C. for 10 to 30 minutes, a catheter body formed of a shape memory alloy (having both shape memory property and superelasticity or pseudoelasticity) was fabricated (Comparative Example 1).

Each of the catheter bodies of Example 1 and Comparative Example 1 was tested as shown in FIG. 1. A distal end portion of the catheter body which extended 15 cm from the distal end was supported on a rubber plate and deformed an angle (of 90 degrees, then the deforming force was relieved. The catheter body of Example 1 moderately (or gradually) restored in about 2 seconds at the body temperature (typically about 33 to 42° C., and preferably in the range of 35 to 38° C.). By contrast the catheter body of Comparative Example 1 instantaneously restored in less than 0.3 second.

The yield force, recovery force, and residual strain were measured by a three-point bending test as specified below. The results are shown in Table 1.

Three-point Bending Test

As shown in FIG. 2, the catheter body was set at fulcrums (a) to (d). At each measurement point, the yield force and recovery force at a displacement of 1 mm were measured, and the residual strain was determined from a residual displacement after load release.

| Measurement conditions | |
| --- | --- |
| Test speed: | 2 mm/min. |
| Punch tip shape: | 5 mm diameter |
| Fulcrum shape (a to d): | 6 mm diameter |
| Fulcrum distance (a–b): | 18 mm |
| Fulcrum distance (c–d): | 14 mm |
| Punch displacement: | 2 mm |
| Measurement temperature: | 37 ± 1° C. |

TABLE 1

| | Measurement point, length from distal end (mm) | Yield force (dy = 1 mm, N) | Recovery force (dy = 1 mm, N) | Residual strain (mm) |
| --- | --- | --- | --- | --- |
| Example 1 | 37.5 | 4.4 | 0 | 1.33 |
| | 125 | 5.9 | 0 | 1.06 |
| | 250 | 8.1 | 2.1 | 0.13 |
| | 325 | 8.9 | 3.9 | 0.03 |
| CE 1 | distal end to 325 | ≧8.9 | ≧3.0 | <0.2 |

Then, a thermoplastic polymer was coated onto the inner and outer surfaces of each of the catheter bodies of Example 1 and Comparative Example 1, completing catheters.

To take advantage of the rigidity or torque of a proximal end portion, a distal end portion of the catheter of Example 1 was rounded to a radius (R) of about 1 mm (arteriola) to about 50 mm (aortic arch) and shape memorized within the range of 0 to 120 degrees, especially 30 to 90 degrees.

The catheters of Example 1 could be smoothly introduced into blood vessels. The catheter body was supple and highly flexible. Since the distal end portion of 1 to 50 mm long is formed to such an angle that after entry into the desired blood vessel, the catheter can be smoothly inserted further, it causes no damage to the blood vessel. Additionally, the distal end portion of the catheter body does not have superelasticity or pseudoelasticity, and in this regard too, the catheter minimizes damage to the blood vessel. Even when folded or bent, the distal end portion of the catheter body has the shape memory effect of effecting gradual and spontaneous recovery at the body temperature of 36 to 37° C. It is noted that the catheter can be operated without a need for a guide wire since the proximal end portion of the catheter has sufficient rigidity.

In contrast, especially because the distal end portion has superelasticity or pseudoelasticity, the catheter of Comparative Example 1 has high rigidity so that it is inserted with difficulty into a tortuous thin wall vessel or duct. Forced insertion of the catheter can cause damage to the blood vessel or duct. This catheter is poor in operability and safety.

Example 2

A catheter of Example 2 was fabricated by joining a thermoplastic resin tube of about 5 cm long to the distal end of the catheter body of Example 1. A metal wire was externally wound around the joint between the thermoplastic resin tube and the catheter body and the vicinity thereof in a coil fashion to form a reinforcement. A thermoplastic resin was coated onto the outer surfaces of the catheter body and the thermoplastic resin tube. It is noted that an inner polymer layer was formed on the inner surface of the catheter body by coating a thermoplastic polymer.

The catheter of Example 2 can be smoothly introduced into a blood vessel because no step-like structure is formed at the joint between the introducing tube made of thermoplastic resin and the catheter body and in the vicinity thereof.

Example 3

A catheter of Example 3 having a radially or outwardly dilatable space at the distal end and discharge lumen at the distal end face (lid) of the catheter was fabricated by the method shown in FIGS. 17(A) to 17(C) involving coating and forming inner and outer polymer layers on the inner and outer surfaces of the catheter body of Example 1, respectively.

On use of this catheter, when its distal end reaches the destination within the living body, a predetermined amount of an embolic material is injected from an operating unit through the catheter lumen to fill the space therewith whereby the catheter distal end portion is dilated outward to block the blood flow through the blood vessel. In this state, the embolic material is discharged through the discharge lumen open at the distal end face of the catheter. In this way, embolization of the lesion is effected in a safe and reliable manner.

Example 4

A tubular body of a Ni—Ti alloy with a nickel content of 49 to 58 atomic % was cold worked and drawn in a conventional manner, forming a catheter body having an outer diameter of 725 μm, an inner diameter of 625 μm, and a thickness of 50 μm. The catheter body was heated treated at 400° C. for 10 to 30 minutes. A distal end portion of the catheter body which extended 30 cm from the distal end was heat treated in argon gas at 400° C. for 24 hours.

The treated catheter body was tested as shown in FIG. 1. A distal end portion of the catheter body which extended 15 cm from the distal end was deformed an angle (of 90 degrees, then the deforming force was relieved. The catheter body moderately (or gradually) restored in about 2 seconds at the body temperature. A three-point bending test was similarly carried out, with the results shown in Table 2.

Example 5

A tubular body of a Ni—Ti alloy with a nickel content of 49 to 58 atomic % was cold worked and drawn in a conventional manner, forming a catheter body having an outer diameter of 600 μm, an inner diameter of 500 μm, and a thickness of 50 μm. The catheter body was heat-treated at 400° C. for 10 to 30 minutes. A distal end portion of the catheter body which extended 30 cm from the distal end was heat-treated in argon gas at 400° C. for 24 hours.

The treated catheter body was tested as shown in FIG. 1. A distal end portion of the catheter body which extended 15 cm from the distal end was deformed an angle (of 90 degrees, then the deforming force was relieved. The catheter body moderately (or gradually) restored in about 2 seconds at the body temperature. A three-point bending test was similarly carried out, with the results shown in Table 2.

Example 6

A tubular body of a Ni—Ti alloy with a nickel content of 49 to 58 atomic % was cold worked and drawn in a conventional manner, forming a catheter body having an outer diameter of 320 μm, an inner diameter of 220 μm, and a thickness of 50 μm. The catheter body was heated treated at 400° C. for 10 to 30 minutes. A distal end portion of the catheter body which extended 30 cm from the distal end was heat treated in argon gas at 400° C. for 24 hours.

The treated catheter body was tested as shown in FIG. 1. A distal end portion of the catheter body which extended 15 cm from the distal end was deformed an angle (of 90 degrees, then the deforming force was relieved. The catheter body moderately (or gradually) restored in about 2 seconds at the body temperature. A three-point bending test was similarly carried out, with the results shown in Table 2.

TABLE 2

| | Measurement point, length from distal end (mm) | Yield force (dy = 1 mm, N) | Recovery force (dy = 1 mm, N) | Residual strain (mm) |
|---|---|---|---|---|
| Example 4 | 37.5 | ≦2.9 | ≦0.1 | ≧0.9 |
| Example 5 | 37.5 | ≦2.0 | ≦0.1 | ≧0.9 |
| Example 6 | 37.5 | ≦2.0 | ≦0.1 | ≧0.9 |

Then, a thermoplastic polymer was coated onto the inner and outer surfaces of each of the catheter bodies of Examples 4 to 6, completing catheters.

The resulting catheters were supple and highly flexible and could be smoothly introduced into blood vessels without causing damage to the blood vessels.

Examples 7 and 8

Catheter bodies having an inner diameter of 600 μm (Example 7) and 500 μm (Example 8) were fabricated from the catheter bodies (inner diameter 750 μm) of Example 1 by the method shown in FIGS. 28(A) to 28(C) involving cutting in the catheter body four slits of wedge shape in side elevation which extended 20 cm from the distal end of the catheter body. A thermoplastic polymer was then coated onto the inner and outer surfaces of each of the catheter bodies, completing catheters.

The catheters of Examples 7 and 8 can be smoothly introduced into blood vessels. The catheter bodies are supple and highly flexible and especially, the distal end portion of the catheters lacks superelasticity or pseudoelasticity. In this regard too, the catheter minimizes damage to the blood vessels.

Example 9

A catheter body having an inner diameter of 500 μm was fabricated from the catheter body (inner diameter 625 μm) of Example 4 by the method shown in FIGS. 28(A) to 28(C) involving cutting in the catheter body four slits of wedge shape in side elevation which extended 20 cm from the distal end of the catheter body. A thermoplastic polymer was then coated onto the inner and outer surfaces of the catheter body, completing a catheter.

The resulting catheter is supple and of quality, especially because its distal end portion is highly flexible.

Example 10

A catheter body having an inner diameter of 400 μm was fabricated from the catheter body (inner diameter 500 μm) of Example 5 by the method shown in FIGS. 28(A) to 28(C) involving cutting in the catheter body four slits of wedge shape in side elevation which extended 20 cm from the distal end of the catheter body. A thermoplastic polymer was then coated onto the inner and outer surfaces of the catheter body, completing a catheter.

The resulting catheter is supple and of quality, especially because its distal end portion is highly flexible.

Example 11

A catheter body having a very small inner diameter of 150 μm was fabricated from the catheter body (inner diameter 220 μm) of Example 6 by the method shown in FIGS. 28(A) to 28(C) involving cutting in the catheter body four slits of wedge shape in side elevation which extended 20 cm from the distal end of the catheter body. A thermoplastic polymer was then coated onto the inner and outer surfaces of the catheter body, completing a catheter.

The resulting catheter is supple and of quality, especially because its distal end portion is highly flexible.

What is claimed is:

1. A catheter characterized in that at least a distal end portion of a catheter body is formed of a shape memory-specialized alloy having shape memory property, but free from superelasticity or pseudoelasticity at least at a body temperature, and the distal end portion made of the shape memory-specialized alloy is shape memorized to a circular arc such that it may recover its memory-shape with a local radius of curvature along the distal end portion in the range of 200 mm to less than ∞ mm at the body temperature.

2. A catheter characterized in that at least a distal end; portion of a catheter body is formed of a shape memory-specialized alloy having shape memory property, but free from superelasticity or pseudoelasticity at least at a body temperature, and when at least a distal end portion of said catheter body is deformed at an angle of 30 to 90 degrees at the body temperature, it takes not less than 0.3 seconds to recover upon unload of the deforming force.

3. A catheter characterized in that at least a distal end portion of a catheter body is formed of a shape memory-specialized alloy having shape memory property, but free from superelasticity or pseudoelasticity at least at a body temperature, and at least a distal end portion of said catheter body is formed of a metal material which has a yield force of not higher than 8.8 N, a recovery force of not higher than 2.9 N and a residual strain of not lower than 0.2 mm when a three-point bending test is carried out using a cylindrically shaped tube entirely made of the metal material having an outer diameter of 875 μm and an inner diameter of 750 μm.

4. A catheter characterized in that at least a distal end portion of a catheter body is formed of a shape memory-specialized alloy having shape memory property, but free from superelasticity or pseudoelasticity at least at a body temperature, at least the distal end portion of the catheter body is prepared from heat treating a Ni—Ti base shape memory alloy having shape memory property and superelasticity or pseudoelasticity at least at the body temperature so that said Ni—Ti base shape memory alloy is converted into a shape memory-specialized alloy in which the superelasticity or pseudoelasticity of the shape memory alloy is non-existent with its shape memory property maintained, and at least the distal portion of the catheter body is deformed at an angle of 30 to 90 degrees at least at the body temperature and when deforming force is unloaded, restoration takes a time of not shorter than 0.5 seconds.

5. The catheter of claim 1, 2, 3 or 4 wherein the catheter body is entirely formed of said shape memory-specialized alloy.

6. The catheter of claim 1, 2, 3 or 4 wherein the distal end portion of the catheter body is formed of said shape memory-specialized alloy, and a remainder of the catheter body is formed of a shape memory alloy having shape memory property and superelasticity or pseudoelasticity at least at the body temperature.

7. The catheter of claim 1, 2, 3 or 4 wherein the distal end portion made of the shape memory-specialized alloy is tapered.

8. The catheter of claim 1, 2, 3 or 4 wherein the distal end portion made of the shape memory-specialized alloy is shape memorized to an angle segment such that it may recover a memory-shape with an angle in the range of 0 to 120 degrees at the body temperature.

* * * * *